(12) United States Patent
Elder et al.

(10) Patent No.: US 7,504,354 B2
(45) Date of Patent: Mar. 17, 2009

(54) ORGANOMETALLIC TRANSITION METAL COMPOUND, BISCYCLOPENTADIENYL LIGAND SYSTEM, CATALYST SYSTEM AND PROCESS FOR PREPARING POLYOLEFINS

(75) Inventors: Michael J. Elder, Rockville, MD (US); Robert L. Jones, Oakland, CA (US); John A. Ewen, Lake Placid, FL (US)

(73) Assignee: Basell Polyolefine GmbH, Wesseling (DE)

( * ) Notice: Subject to any disclaimer, the term of this patent is extended or adjusted under 35 U.S.C. 154(b) by 39 days.

(21) Appl. No.: 10/578,059

(22) PCT Filed: Nov. 2, 2004

(86) PCT No.: PCT/EP2004/012358

§ 371 (c)(1), (2), (4) Date: Jun. 11, 2007

(87) PCT Pub. No.: WO2005/044870

PCT Pub. Date: May 19, 2005

(65) Prior Publication Data

US 2007/0260025 A1    Nov. 8, 2007

Related U.S. Application Data

(60) Provisional application No. 60/528,591, filed on Dec. 11, 2003.

(30) Foreign Application Priority Data

Nov. 4, 2003 (DE) ................... 103 52 139

(51) Int. Cl.
C08F 4/6592 (2006.01)
C08F 4/642 (2006.01)
(52) U.S. Cl. ............. 502/155; 502/103; 526/160; 526/161; 526/165
(58) Field of Classification Search ........ 502/103, 502/152, 155; 526/160, 161, 165
See application file for complete search history.

(56) References Cited

U.S. PATENT DOCUMENTS

| 5,455,365 A | 10/1995 | Winter et al. |
| 5,455,366 A | 10/1995 | Rohrmann et al. |
| 5,830,821 A | 11/1998 | Rohrmann et al. |
| 6,417,302 B1 | 7/2002 | Bohnen |
| 6,589,905 B1 | 7/2003 | Fischer et al. |

FOREIGN PATENT DOCUMENTS

| EP | 0 549 900 | 7/1993 |
| EP | 0 582 194 | 2/1994 |
| EP | 1 327 636 | 7/2003 |
| WO | WO-91/09882 | 7/1991 |
| WO | WO-96/00243 | 1/1996 |
| WO | WO-98/40419 | 9/1998 |
| WO | WO-99/06414 | 2/1999 |
| WO | WO-00/05277 | 2/2000 |
| WO | WO-00/31090 | 6/2000 |
| WO | WO-03/045964 | 6/2003 |
| WO | WO-03/106470 | 12/2003 |

OTHER PUBLICATIONS

Ryabov, Alexey N. et al., "Zirconium Complexes with Cyclopentadienyl Ligands Involving Fused a Thiophene Fragment", Organometallics 21 (2002), pp. 2842-2855.
Kloetzel, Milton C. et al., "Synthesis of 4-Substituted Thianaphthene Derivatives", J. Organic Chem 19 (1953), pp. 1511-1515.

*Primary Examiner*—Caixia Lu
(74) *Attorney, Agent, or Firm*—William R. Reid; Jarrod N. Raphael; Jonathan L. Schuchardt

(57) ABSTRACT

The present invention relates to organometallic transition metal compounds of the formula (I), a catalyst composition comprising at least one of the organometallic transition metal compound and an olefin polymerization process in the presence of one of the catalyst composition.

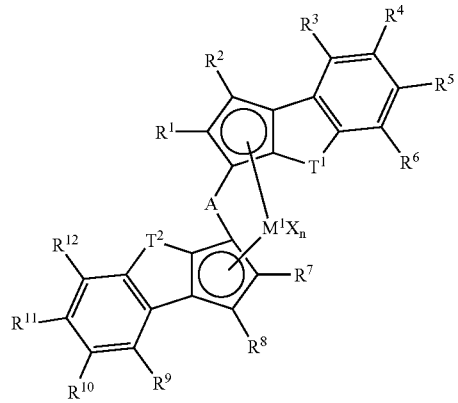

6 Claims, 1 Drawing Sheet

Figure 1A:
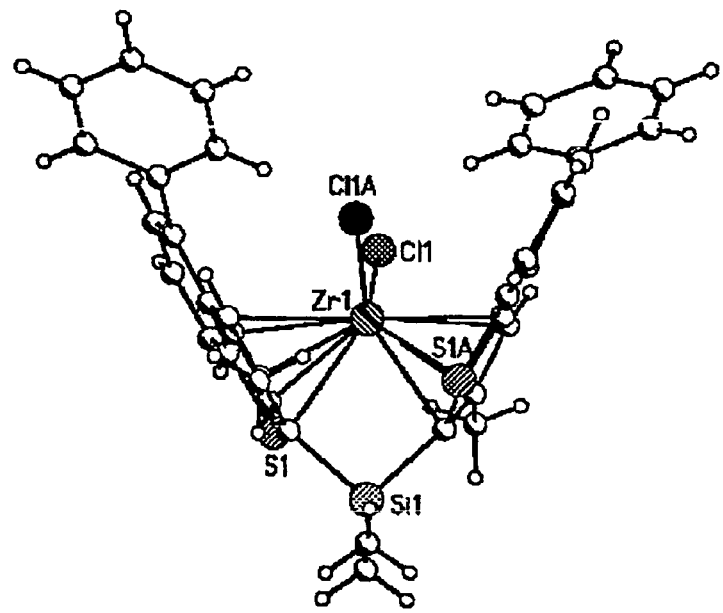

ORGANOMETALLIC TRANSITION METAL COMPOUND, BISCYCLOPENTADIENYL LIGAND SYSTEM, CATALYST SYSTEM AND PROCESS FOR PREPARING POLYOLEFINS

RELATED APPLICATIONS

This application is a national stage application (under 35 U.S.C. 371) of PCT/EP2004/012358 filed Nov. 2, 2004 which claims benefit to German application 103 52 139.9 filed Nov. 4, 2003 and United States provisional application 60/528,591 filed Dec. 11, 2003.

The present invention relates to organometallic transition metal compounds of the formula (I)

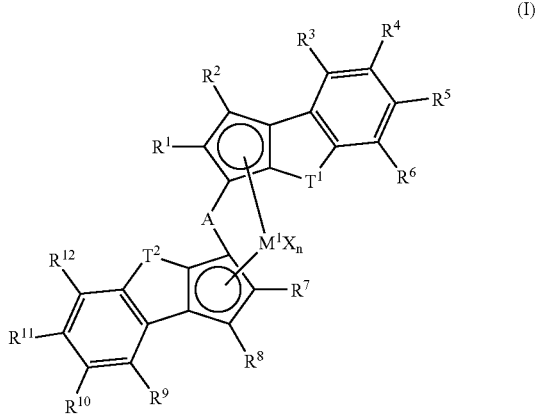

where $M^1$ is an element of group 3, 4, 5 or 6 of the Periodic Table of the Elements or the lanthanides, X are identical or different and are each an organic or inorganic radical, where two radicals X can also be joined to one another, n is a natural number from 1 to 4, $T^1$, $T^2$ are identical or different and are each a divalent group selected from the group consisting of —O—, —S—, —Se—, —Te—, —N($R^{13}$)—, —P($R^{13}$)—, —As($R^{13}$)—, —Sb($R^{13}$)—, —Si($R^3$)$_2$—, —C($R^{13}R^{14}$)—C($R^{13}R^{15}$)— and —C($R^{14}$)=C($R^{15}$)—, where $R^{13}$, $R^{14}$ and $R^{15}$ are identical or different and are each hydrogen or an organic radical having from 1 to 40 carbon atoms, $R^1$, $R^7$ are identical or different and are each hydrogen or an organic radical having from 1 to 40 carbon atoms, $R^2$, $R^8$ are identical or different and are each hydrogen or an organic radical having from 1 to 40 carbon atoms, $R^3$, $R^9$ are identical or different and are each halogen or an organic radical having from 1 to 40 carbon atoms, where $R^3$ is not methyl when $T^1$ is —C(H)=C(H)—, $R^4$, $R^5$, $R^6$, $R^{10}$, $R^{11}$ and $R^{12}$ are identical or different and are each hydrogen, halogen or an organic radical having from 1 to 40 carbon atoms, or two adjacent radicals $R^4$, $R^5$, $R^6$, $R^{10}$, $R^{11}$ and $R^{12}$ together with the atoms connecting them form a monocyclic or polycyclic, substituted or unsubstituted ring system which has from 1 to 40 carbon atoms and may also contain heteroatoms selected from the group consisting of the elements O, S, Se, Te, N, P, As, Sb and Si, or, if $T^1$ or $T^2$ is —O—, —S—, —Se— or —Te—, the radical $R^3$ together with $R^4$ and/or the radical $R^9$ together with $R^{10}$ form a monocyclic or polycyclic, substituted or unsubstituted ring system which has from 1 to 40 carbon atoms and may also contain heteroatoms selected from the group consisting of the elements O, S, Se, Te, N, P, As, Sb and Si, and A is a bridge consisting of a divalent atom or a divalent group.

In addition, the present invention relates to biscyclopentadienyl ligand systems having such a substitution pattern, catalyst systems comprising at least one of the organometallic transition metal compounds of the present invention, a process for preparing polyolefins by polymerization or copolymerization of at least one olefin in the presence of one of the catalyst systems of the present invention and the polyolefins obtainable in this way, the use of the biscyclopentadienyl ligand systems of the present invention for preparing organometallic transition metal compounds and a process for preparing organometallic transition metal compounds using the biscyclopentadienyl ligand systems.

Research and development on the use of organometallic transition metal compounds, in particular metallocenes, as catalyst components for the polymerization and copolymerization of olefins with the aim of preparing tailored polyolefins has been pursued intensively in universities and industry over the past 15 years. In addition to the ethylene-based polyolefins prepared by means of metallocene catalyst systems, propylene-based polyolefins in particular prepared by means of metallocene catalyst systems are now a dynamically growing market segment.

The use of soluble metallocene compounds based on bis (cyclopentadienyl)dialkylzirconium or bis(cyclopentadienyl) dihalide in combination with aluminoxanes give atactic polypropylenes.

Bisindenyl-substituted ansa-metallocenes have been optimized in respect of, in particular, their ability to produce highly isotactic polypropylenes having a high crystallinity and a high melting point. Furthermore, bisindenyl-substituted ansa-metallocenes which are suitable both for preparing highly isotactic polypropylenes and for preparing high molecular weight propylene-ethylene copolymers which are used, for example, as rubber phase in the production of impact-modified polypropylene polymers have been found.

Organometallics 2002, 21, 2842-2855, describes metallocenes whose cyclopentadienyl ligands contain fused-on thiophene fragments. These metallocenes were not converted further into polymerization catalysts or tested as such.

EP 549900 describes benzo-fused bisindenyl metallocenes which when used as catalyst components allow the preparation of highly isotactic polypropylenes having an industrially relevant molar mass.

EP 582194 describes bisindenyl-substituted ansa-metallocenes having a specific substitution pattern, by means of which polypropylenes having a reduced isotacticity can be obtained.

However, there is a need for metallocene structures which not only make it possible to obtain polypropylenes having an even lower isotacticity while retaining a high molar mass but also allow the preparation of high molecular weight propylene-ethylene copolymers. There is also a need for metallocene structures which allow the reduced isotacticity of the desired polypropylenes to be controlled in a simple fashion. Furthermore, these metallocenes should also make it possible to prepare high molecular weight, crystalline polyethylenes having a high density.

The known metallocene catalyst systems are still in need of improvement in respect of the property profile described. A further aspect in the search for new catalyst systems and catalyst components is always the ability to obtain the new catalyst systems and catalyst components in an economical way and to provide an economical and environmentally friendly process for preparing polyolefins.

It is an object of the present invention to find new organometallic transition metal compounds which, when used as catalyst component for olefin polymerization, avoid the disadvantages of the prior art and make it possible for the polymerization behavior and the polymer properties to be controlled in a targeted way.

We have found that this object is achieved by the organometallic transition metal compounds of the formula (I) mentioned at the outset.

$M^1$ is an element of group 3, 4, 5 or 6 of the Periodic Table of the Elements or the lanthanides, for example titanium, zirconium, hafnium, vanadium, niobium, tantalum, chromium, molybdenum or tungsten, preferably titanium, zirconium, hafnium, particularly preferably zirconium or hafnium and very particularly preferably zirconium.

X are identical or different, preferably identical, and are each an organic or inorganic radical, where two radicals X may also be joined to one another. X is preferably halogen, for example fluorine, chlorine, bromine, iodine, preferably chlorine, hydrogen, $C_1$-$C_{20}$—, preferably $C_1$-$C_4$-alkyl, in particular methyl, $C_2$-$C_{20}$—, preferably $C_2$-$C_4$-alkenyl, $C_6$-$C_{22}$—, preferably $C_6$-$C_{10}$-aryl, an alkylaryl or arylalkyl group having from 1 to 10, preferably from 1 to 4 carbon atoms in the alkyl part and from 6 to 22, preferably from 6 to 10, carbon atoms in the aryl part, —$OR^{16}$ or —$NR^{16}R^{17}$, preferably —$OR^{16}$, where two radicals X may also be joined to one another, preferably two radicals —$OR^{16}$. Two radicals X may also form a substituted or unsubstituted diene ligand, in particular a 1,3-diene ligand. The radicals $R^{16}$ and $R^{17}$ are each $C_1$-$C_{10}$—, preferably $C_1$-$C_4$-alkyl, $C_6$-$C_{15}$—, preferably $C_6$-$C_{10}$-aryl, alkylaryl, arylalkyl, fluoroalkyl or fluoroaryl each having from 1 to 10, preferably from 1 to 4, carbon atoms in the alkyl radical and from 6 to 22, preferably from 6 to 10, carbon atoms in the aryl radical.

Unless restricted further, alkyl is a linear, branched or cyclic radical such as methyl, ethyl, n-propyl, isopropyl, n-butyl, i-butyl, s-butyl, t-butyl, n-pentyl, cyclopentyl, n-hexyl, cyclohexyl, n-heptyl or n-octyl.

The index n is a natural number from 1 to 4 which is frequently equal to the oxidation number of $M^1$ minus 2. In the case of the elements of group 4 of the Periodic Table of the Elements, n is preferably 2.

$T^1$ and $T^2$ are identical or different, preferably identical, and are each a divalent group selected from the group consisting of —O—, —S—, —Se—, —Te—, —N($R^{13}$)—, —P($R^{13}$)—, —As($R^{13}$)—, —Sb($R^{13}$)—, —Si($R^{13}$)$_2$—, —C($R^{13}R^{14}$)—C($R^{13}R^{13}$)— and —C($R^{14}$)=C($R^{15}$)—, preferably —O—, —S— and —Se—, in particular —S—, where $R^{13}$, $R^{14}$ and $R^{15}$ are identical or different and are each hydrogen or an organic radical having from 1 to 40 carbon atoms. Preferred examples of the radicals $R^{13}$, $R^{14}$ and $R^{15}$ are hydrogen, cyclic, branched or unbranched $C_1$-$C_{20}$—, preferably $C_1$-$C_8$-alkyl radicals, $C_2$-$C_{20}$—, preferably $C_2$-$C_8$-alkenyl radicals, $C_6$-$C_{22}$—, preferably $C_6$-$C_{10}$-aryl radicals, alkylaryl or arylalkyl radicals having from 1 to 10, preferably from 1 to 4, carbon atoms in the alkyl part and from 6 to 22, preferably from 6 to 10, carbon atoms in the aryl part, where the radicals may also be halogenated or the radicals $R^{13}$, $R^{14}$ and $R^{15}$ can also be substituted or unsubstituted, saturated or unsaturated, in particular aromatic, heterocyclic radicals which have from 2 to 40, in particular from 4 to 20, carbon atoms and contain at least one heteroatom, preferably a heteroatom selected from the group of elements consisting of O, N, S and P, in particular N. Particular preference is given to $R^{14}$ and $R^{15}$ each being hydrogen or methyl, in particular hydrogen.

$R^1$ and $R^7$ are identical or different, preferably identical, and are each hydrogen or an organic radical having from 1 to 40 carbon atoms, for example $C_1$-$C_{40}$-alkyl, $C_1$-$C_{10}$-fluoroalkyl, $C_2$-$C_{40}$-alkenyl, $C_6$-$C_{40}$-aryl, $C_6$-$C_{10}$-fluoroaryl, arylalkyl, arylalkenyl or alkylaryl having from 1 to 10, preferably from 1 to 4, carbon atoms in the alkyl part and from 6 to 22, preferably from 6 to 10, carbon atoms in the aryl part, or a $C_2$-$C_{40}$-heteroaromatic radical containing at least one heteroatom selected from the group consisting of the elements O, N, S, P and Se, in particular O, N and S, where the heteroaromatic radical may be substituted by further radicals $R^{18}$, where $R^{18}$ is an organic radical having from 1 to 20 carbon atoms and is, in particular, defined like $R^{16}$, and a plurality of radicals $R^{18}$ may be identical or different.

$R^1$ and $R^7$ are preferably hydrogen, a cyclic, branched or unbranched, preferably unbranched, $C_1$-$C_{20}$—, preferably $C_1$-$C_{10}$-alkyl radical, a $C_6$-$C_{22}$—, preferably $C_6$-$C_{14}$-aryl radical, an arylalkyl or alkylaryl radical having from 1 to 10, preferably from 1 to 4, carbon atoms in the alkyl part and from 6 to 22, preferably from 6 to 10, carbon atoms in the aryl part, or a $C_4$-$C_{24}$-heteroaromatic radical selected from the group consisting of substituted or unsubstituted thienyl radicals, substituted or unsubstituted furyl radicals and substituted or unsubstituted pyrrolyl radicals, where the substituents on the five-membered heteroaromatic radicals are preferably $C_1$-$C_4$-alkyl radicals or $C_6$-$C_{20}$—, preferably $C_6$-$C_{10}$-aryl radicals, in particular methyl, ethyl or phenyl.

Particular preference is given to $R^1$ and $R^7$ being unbranched $C_1$-$C_{10}$-alkyl radicals, in particular methyl, ethyl, n-propyl or n-hexyl.

$R^2$ and $R^8$ are identical or different, preferably identical, and are each hydrogen or an organic radical having 1 to 40 carbon atoms, for example $C_1$-$C_{40}$-alkyl, $C_1$-$C_{10}$-fluoroalkyl, $C_2$-$C_{40}$-alkenyl, $C_6$-$C_{40}$-aryl, $C_6$-$C_{10}$-fluoroaryl, arylalkyl, arylalkenyl or alkylaryl having from 1 to 10, preferably from 1 to 4, carbon atoms in the alkyl part and from 6 to 22, preferably from 6 to 10, carbon atoms in the aryl part, or a $C_2$-$C_{40}$-heteroaromatic radical containing at least one heteroatom selected from the group consisting of the elements O, N, S, P and Se, in particular O, N and S, where the heteroaromatic radical may be substituted by further radicals $R^{18}$, where $R^{18}$ is an organic radical having from 1 to 20 carbon atoms and is, in particular, defined like $R^{16}$, and a plurality of radicals $R^{18}$ may be identical or different.

$R^2$ and $R^8$ are preferably hydrogen.

$R^3$ and $R^9$ are identical or different, preferably identical, and are each halogen such as fluorine, chlorine, bromine or iodine, in particular fluorine or chlorine, or an organic radical having from 1 to 40, in particular from 3 to 40, carbon atoms, for example $C_1$-$C_{40}$-alkyl, $C_1$-$C_{10}$-fluoroalkyl, $C_2$-$C_{40}$-alkenyl, $C_6$-$C_{40}$-aryl, $C_6$-$C_{10}$-fluoroaryl, arylalkyl, arylalkenyl or alkylaryl having from 1 to 10, preferably from 1 to 4, carbon atoms in the alkyl part and from 6 to 22, preferably from 6 to 10, carbon atoms in the aryl part, or a $C_2$-$C_{40}$-heterocyclic, in particular heteroaromatic, radical containing at least one heteroatom selected from the group consisting of the elements O, N, S, P and Se, in particular O, N and S, where the heterocyclic radical may be substituted by further radicals $R^{18}$, where $R^{18}$ is an organic radical having from 1 to 20 carbon atoms and is, in particular, defined like $R^{16}$, and a plurality of radicals $R^{16}$ may be identical or different, where $R^3$ is not methyl when $T^1$ is —C(H)=C(H)—.

$R^3$ and $R^9$ are preferably each organic radicals which are branched in the a position and have from 3 to 40 carbon atoms, where a radical branched in the α position is one whose linking α atom bears at least two directly bound atoms which are not hydrogen and not more than one directly bound hydrogen atom. The linking α atom is preferably carbon.

The radicals $R^3$ and $R^9$ are particularly preferably $C_3$-$C_{20}$—, preferably $C_3$-$C_{10}$-alkyl, $C_3$-$C_{20}$—, preferably $C_3$-$C_8$-alkenyl, $C_6$-$C_{22}$—, preferably $C_6$-$C_{10}$-aryl, alkylaryl, arylalkyl or arylalkenyl each having from 1 to 10, preferably from 1 to 4, carbon atoms in the alkyl part and from 6 to 22, preferably from 6 to 10, carbon atoms in the aryl part, $C_3$-$C_{12}$—, preferably $C_5$-$C_8$-cycloalkyl or cycloalkenyl, or the radicals $R^3$ and $R^9$ are each saturated or unsaturated heterocyclic radicals having from 3 to 10 carbon atoms and at least one heteroatom selected from the group consisting of the elements O, N, S, P and Si, preferably O, N and S, where carbocyclic or heterocyclic radicals may be substituted by further radicals $R^{18}$, where $R^{18}$ is an organic radical having from 1 to 20 carbon atoms and is, in particular, defined like $R^{16}$, and a plurality of radicals $R^{18}$ may be identical or different. Examples of preferred radicals $R^3$ and $R^9$ are isopropyl, cyclobutyl, 1-methylpropyl, 1-methylbutyl, 1-ethylbutyl, 1-methylpentyl, cyclopentyl, cyclohexyl, t-butyl, cyclopent-2-enyl, cyclopent-3-enyl, cyclohex-2-enyl, cyclohex-3-enyl, para-methylcyclohexyl, diphenylmethyl, triphenylmethyl, phenyl, 2-tolyl, 3-tolyl, 4-tolyl, 2,6-dimethylphenyl, 2,4,6-trimethylphenyl, 1-naphthyl, 2-naphthyl, phenanthyl, thienyl, furyl, methylthienyl, methylfuryl, trifluoromethyl or trimethylsilyl.

$R^4$, $R^5$, $R^6$, $R^{10}$, $R^{11}$ and $R^{12}$ are identical or different and are each hydrogen, halogen such as fluorine, chlorine, bromine or iodine, in particular fluorine or chlorine, or an organic radical having from 1 to 40 carbon atoms, for example $C_1$-$C_{40}$-alkyl, $C_1$-$C_{10}$-fluoroalkyl, $C_2$-$C_{40}$-alkenyl, $C_6$-$C_{40}$-aryl, $C_6$-$C_{10}$-fluoroaryl, arylalkyl, arylalkenyl or alkylaryl each having from 1 to 10, preferably from 1 to 4, carbon atoms in the alkyl part and from 6 to 22, preferably from 6 to 10, carbon atoms in the aryl part, or a $C_2$-$C_{40}$-heterocyclic, in particular heteroaromatic radical containing at least one heteroatom selected from the group consisting of the elements O, N, S, P and Se, in particular O, N and S, where the heterocyclic radical may be substituted by further radicals $R^{18}$, where $R^{18}$ is an organic radical having from 1 to 20 carbon atoms and is, in particular, defined like $R^{16}$, and a plurality of radicals $R^{18}$ may be identical or different; or two adjacent radicals $R^4$, $R^5$, $R^6$, $R^{10}$, $R^{11}$ and $R^{12}$ together with the atoms connecting them may form a monocyclic or polycyclic substituted or unsubstituted ring system which has from 1 to 40, preferably from 4 to 30, carbon atoms and may also contain heteroatoms selected from the group consisting of the elements O, S, Se, Te, N, P, As, Sb and Si, in particular O, N and S.

Preference is given to $R^4$, $R^5$, $R^{10}$ and $R^{11}$ being identical and each being hydrogen and $R^6$ and $R^{12}$ being as defined above.

If $T^1$ or $T^2$ is —O—, —S—, —Se— or —Te—, the radical $R^3$ together with $R^4$ and/or the radical $R^9$ together with $R^{10}$ can form a monocyclic or polycyclic, substituted or unsubstituted ring system which has from 1 to 40 carbon atoms and may also contain heteroatoms selected from the group consisting of the elements O, S, Se, Te, N, P, As, Sb and Si, in particular O, S and N. $R^3$ with $R^4$ and/or $R^9$ with $R^{10}$ together with the two further carbon atoms in each case preferably form 5- and 6-membered ring systems which are preferably aromatic.

A is a bridge consisting of a divalent atom or a divalent group. Examples of A are:

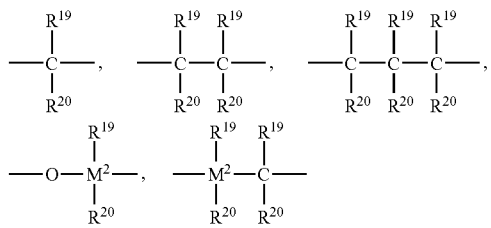

—B($R^{19}$)—, —B(N$R^{19}R^{20}$)—, —Al($R^{19}$)—, —O—, —S—, —S(O)—, —S(O$_2$)—, —N($R^{19}$)—, —C(O)—, —P($R^{19}$)— or —P(O) ($R^{19}$)—,
preferably

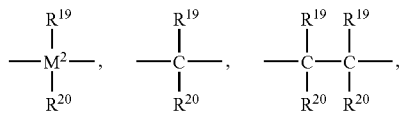

where
$M^2$ is silicon, germanium or tin, preferably silicon or germanium, particularly preferably silicon, and
$R^{19}$, $R^{20}$ and $R^{21}$ are identical or different and are each a hydrogen atom, a halogen atom, a trimethylsilyl group, a $C_1$-$C_{10}$—, preferably $C_1$-$C_3$-alkyl group, a $C_1$-$C_{10}$-fluoroalkyl group, a $C_6$-$C_{10}$-fluoroaryl group, a $C_6$-$C_{10}$-aryl group, a $C_1$-$C_{10}$, preferably $C_1$-$C_3$-alkoxy group, a $C_7$-$C_{15}$-alkylaryloxy group, a $C_2$-$C_{10}$—, preferably $C_2$-$C_4$-alkenyl group, a $C_7$-$C_{40}$-arylalkyl group, a $C_8$-$C_{40}$-arylalkenyl group or a $C_7$-$C_{40}$-alkylaryl group or two adjacent radicals together with the atoms connecting them form a saturated or unsaturated ring having from 4 to 15 carbon atoms.

Particularly preferred examples of A are the bridges:
dimethylsilanediyl, methylphenylsilanediyl, diphenylsilanediyl, dimethylgermanediyl, ethylidene, 1-methylethylidene, 1,1-dimethylethylidene, 1,2-dimethylethylidene, 1,1,2,2-tetramethylethylidene, dimethylmethylidene, phenylmethylmethylidene or diphenylmethylidene, in particular dimethylsilanediyl, diphenylsilanediyl and ethylidene.

The radicals $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$ and $R^{21}$ may, according to the present invention, have further heteroatoms in place of carbon. atoms or hydrogen atoms, in particular heteroatoms selected from the group consisting of Si, N, P, O, S, F and Cl, or functional groups without altering the polymerization properties of the organometallic transition metal compound of the present invention, as long as these heteroatoms or functional groups are chemically inert under the polymerization conditions.

Furthermore, the substituents according to the present invention are, unless restricted further, defined as follows:

The term "organic radical having from 1 to 40 carbon atoms" as used in the present text refers, for example, to $C_1$-$C_{40}$-alkyl radicals, $C_1$-$C_{10}$-fluoroalkyl radicals, $C_1$-$C_{12}$-alkoxy radicals, saturated $C_3$-$C_{20}$-heterocyclic radicals, $C_6$-$C_{40}$-aryl radicals, $C_2$-$C_{40}$-heteroaromatic radicals, $C_6$-$C_{10}$-fluoroaryl radicals, $C_6$-$C_{10}$-aryloxy radicals, $C_3$-$C_{18}$-trialkylsilyl radicals, $C_2$-$C_{20}$-alkenyl radicals, $C_2$-$C_{20}$-alkynyl radicals, $C_7$-$C_{40}$-arylalkyl radicals or $C_8$-$C_{40}$-arylalkenyl radicals. Such an organic radical is in each case derived from an organic compound. Thus, the organic compound methanol can in principle give rise to three different organic radicals having one carbon atom, namely methyl ($H_3C-$), methoxy ($H_3C-O-$) and hydroxymethyl ($HOC(H_2)-$).

The term "alkyl" as used in the present text encompasses linear or singly or multiply branched saturated hydrocarbons which may also be cyclic. Preference is given to $C_1$-$C_{18}$-alkyl, such as methyl, ethyl, n-propyl, n-butyl, n-pentyl, n-hexyl, n-heptyl, n-octyl, n-nonyl, n-decyl, cyclopentyl, cyclohexyl, isopropyl, isobutyl, isopentyl, isohexyl, sec-butyl or tert-butyl.

The term "alkenyl" as used in the present text encompasses linear or singly or multiply branched hydrocarbons each having at least one C—C double bond; in the case of a plurality of double bonds, these can be cumulated or alternating.

The term "saturated heterocyclic radical" as used in the present text refers, for example, to monocyclic or polycyclic, substituted or unsubstituted hydrocarbon radicals in which one or more carbon atoms, CH groups and/or $CH_2$ groups have been replaced by heteroatoms preferably selected from the group consisting of O, S, N and P. Preferred examples of substituted or unsubstituted saturated heterocyclic radicals are pyrrolidinyl, imidazolidinyl, pyrazolidinyl, piperidyl, piperazinyl, morpholinyl, tetrahydrofuranyl, tetrahydropyranyl, tetrahydrothienyl and the like, and also methyl-, ethyl-, propyl-, isopropyl- and tert-butyl-substituted derivatives thereof.

The term "aryl" as used in the present text refers, for example, to aromatic and possibly also fused polyaromatic hydrocarbon substituents which may be monosubstituted or polysubstituted by linear or branched $C_1$-$C_{18}$-alkyl, $C_1$-$C_{18}$-alkoxy or $C_2$-$C_{10}$-alkenyl groups or halogen atoms, in particular fluorine. Preferred examples of substituted and unsubstituted aryl radicals are, in particular, phenyl, pentafluorophenyl, 4-methylphenyl, 4-ethylphenyl, 4-propylphenyl, 4-isopropylphenyl, 4-tert-butylphenyl, 4-methoxyphenyl, 1-naphthyl, 9-anthryl, 9-phenanthryl, 3,5-dimethylphenyl, 3,5-di-tert-butylphenyl or 4-trifluoromethylphenyl.

The term "heteroaromatic radical" as used in the present text refers, for example, to aromatic hydrocarbon radicals in which one or more carbon atoms have been replaced by nitrogen, phosphorus, oxygen or sulfur atoms or combinations thereof. These may, like aryl radicals, be monosubstituted or polysubstituted by linear or branched $C_1$-$C_{18}$-alkyl, $C_2$-$C_{10}$-alkenyl groups or halogen atoms, in particular fluorine; Preferred examples are furyl, thienyl, pyrrolyl, pyridyl, pyrazolyl, imidazolyl, oxazolyl, thiazolyl, pyrimidinyl, pyrazinyl and the like, and also methyl-, ethyl-, propyl-, isopropyl- and tert-butyl-substituted derivatives thereof.

The term "arylalky" as used in the present text refers, for example, to aryl-containing substituents whose aryl radical is linked via an alkyl chain to the remainder of the molecule. Preferred examples are benzyl, substituted benzyl, phenethyl, substituted phenethyl and the like.

The expressions fluoroalkyl and fluoroaryl mean that at least one hydrogen atom, preferably more than one up to a maximum of all hydrogen atoms, of the respective substituents have been replaced by fluorine atoms. Examples of fluorine-containing substituents which are preferred according to the present invention are trifluoromethyl, 2,2,2-trifluoroethyl, pentafluorophenyl, 4-trifluoromethylphenyl, 4-perfluoro-tert-butylphenyl and the like.

Preference is given to organometallic transition metal compounds of the formula (I) in which $M^1$ is an element of group 4 of the Periodic Table of the Elements, preferably zirconium or hafnium, in particular zirconium, n is 2, $T^1$, $T^2$ are identical and are each —O—, —S—, —Se— or —Te—, preferably —O— or —S—, in particular —S—, $R^1$, $R^7$ are identical and are each a $C_1$-$C_{10}$-alkyl radical, for example methyl, ethyl, propyl, isopropyl, n-butyl, n-hexyl, cyclohexyl or n-decyl, preferably methyl or ethyl, in particular methyl, $R^2$, $R^8$ are identical and are each hydrogen, $R^3$, $R^9$ are identical or different and are each a substituted or unsubstituted $C_6$-$C_{40}$-aryl radical or $C_2$-$C_{40}$-heteroaromatic radical having at least one heteroatom selected from the group consisting of O, N, S and P, preferably a substituted or unsubstituted $C_6$-$C_{40}$-aryl radical such as phenyl, 2-tolyl, 3-tolyl, 4-tolyl, 2,3-dimethylphenyl, 2,4-dimethylphenyl, 2,5-dimethylphenyl, 2,6-dimethylphenyl, 3,4-dimethylphenyl, 3,5-dimethylphenyl, 3,5-di(tert-butyl)phenyl, 2,4,6-trimethylphenyl, 2,3,4-trimethylphenyl, 1-naphthyl, 2-naphthyl, phenanthrenyl, p-isopropylphenyl, p-tert-butylphenyl, p-s-butylphenyl, p-cyclohexylphenyl and p-trimethylsilylphenyl, in particular phenyl, 1-naphthyl, 3,5-dimethylphenyl and p-tert-butylphenyl, $R^4$, $R^5$, $R^{10}$ and $R^{11}$ are identical and are each hydrogen, $R^6$, $R^{12}$ are identical and are each hydrogen or an organic radical having from 1 to 20 carbon atoms, for example a cyclic, branched or unbranched $C_1$-$C_{20}$—, preferably $C_1$-$C_{10}$-alkyl radical, a $C_2$-$C_{20}$—, preferably $C_2$-$C_8$-alkenyl radical, an arylalkyl radical having from 1 to 10, preferably from 1 to 4, carbon atoms in the alkyl part and from 6 to 14, preferably from 6 to 10, carbon atoms in the aryl part, preferably hydrogen, methyl, ethyl, n-propyl, isopropyl, n-butyl, i-butyl, s-butyl, t-butyl, phenyl, naphthyl, benzyl or 2-phenylethyl, in particular hydrogen, methyl or isopropyl, A is a substituted silylene group or a substituted or unsubstituted ethylene group, preferably a substituted silylene group such as dimethylsilanediyl, methylphenylsilanediyl, methyl-tert-butylsilanediyl or diphenylsilanediyl, in particular dimethylsilanediyl, and the other variables are as defined in formula (I).

Illustrative but nonlimiting examples of novel organometallic transition metal compounds of the formula (I) are:

[dimethylsilanediyl(2-methyl-8-phenylbenzo[b]cyclopenta[d]-thien-3-ylidene)$_2$]zirconium(IV) dichloride,

[dimethylsilanediyl(2,5-dimethyl-8-phenylbenzo[b]cyclopenta[d]thien-3-ylidene)$_2$]zirconium(IV) dichloride,

[dimethylsilanediyl(2,5,8-trimethylbenzo[b]cyclopenta[d]thien-3-ylidene)$_2$]zirconium(IV) dichloride,

[dimethylsilanediyl(2,5-dimethyl-8-isopropylbenzo[b]cyclopenta[d]thien-3-ylidene)$_2$]zirconium (IV) dichloride,

[dimethylsilanediyl(2-methyl-8-chlorobenzo[b]cyclopenta[d]thien-3-ylidene)$_2$]zirconium(IV) dichloride,

[dimethylsilanediyl(2-methyl-8-isopropylbenzo[b]cyclopenta[d]thien-3-ylidene)$_2$]zirconium(IV) dichloride,

[dimethylsilanediyl(2,8-dimethylbenzo[b]cyclopenta[d]thien-3-ylidene)$_2$]zirconium(IV) dichloride,

[dimethylsilanediyl(2-methyl-8-cyclopentylbenzo[b]cyclopenta[d]thien-3-ylidene)$_2$]zirconium(IV) dichloride,

[dimethylsilanediyl(2-methyl-8-tolylbenzo[b]cyclopenta[d]thien-3-ylidene)$_2$]zirconium(IV) dichloride,

[dimethylsilanediyl(2-methyl-8-methoxybenzo[b]cyclopenta[d]thien-3-ylidene)$_2$]zirconium(IV) dichloride,

[dimethylsilanediyl(2-methyl-8-sec-butylbenzo[b]cyclopenta[d]thien-3-ylidene)$_2$]zirconium(IV) dichloride,

[dimethylsilanediyl(2-methyl-8-phenyl-5,6,7,8-tetrahydrobenzo[b]cyclopenta[d]thien-3-ylidene)$_2$]zirconium(IV) dichloride,

[dimethylsilanediyl(2-methyl-8-phenylbenzo[b]cyclopenta[d]thien-3-ylidene)-(2,8-dimethylbenzo[b]cyclopenta[d]thien-3-ylidene)]zirconium(IV) dichloride,

[dimethylsilanediyl(2-isopropyl-8-phenylbenzo[b]cyclopenta[d]thien-3-ylidene)-(2,8-dimethylbenzo[b]cyclopenta[d]thien-3-ylidene)]zirconium(IV) dichloride,

[dimethylsilanediyl(2-isopropyl-8-methylbenzo[b]cyclopenta[d]thien-3-ylidene)-(2-methyl-8-phenylbenzo[b]cyclopenta[d]thien-3-ylidene)]zirconium(IV) dichloride,

[dimethylsilanediyl([8-methyl-2-(5-methyl-furan-2-yl)benzo[b]cyclopenta[d]thien-3-ylidene)-(2,8-dimethylbenzo[b]cyclopenta[d]thien-3-ylidene)]zirconium(IV) dichloride,

[dimethylsilanediyl([8-methyl-2-(5-methyl-furan-2-yl)benzo[b]cyclopenta[d]thien-3-ylidene)-(2-methyl-8-phenyl-benzo[b]cyclopenta[d]thien-3-ylidene)]zirconium(IV) dichloride,

[dimethylsilanediyl(2-methyl-8-phenylbenzo[b]cyclopenta[d]thien-3-ylidene)-(2,5-dimethyl-3-phenyl-6H-cyclopenta[b]thien-6-ylidene)]zirconium(IV) dichloride,

[dimethylsilanediyl(2-methyl-8-phenylbenzo[b]cyclopenta[d]thien-3-ylidene)-((2-methyl-cyclopenta[a]naphthalen-3-ylidene)]zirconium(IV) dichloride,

[dimethylsilanediyl(9-methyl-7-thiapentaleno[1,2-a]naphthalen-8-ylidene)$_2$]zirconium(IV) dichloride,

[dimethylsilanediyl(2,9-dimethylcyclopenta[a]naphthalen-3-ylidene)$_2$]zirconium(IV) dichloride,

[dimethylsilanediyl(2,6,9-trimethylcyclopenta[a]naphthalen-3-ylidene)$_2$]zirconium(IV) dichloide,

[dimethylsilanediyl(2,6,9-trimethyl-4,5-dihydrocyclopenta[a]naphthalen-3-ylidene)$_2$]zirconium(IV) dichloride,

[dimethylsilanediyl(2,4-dimethyl-8-phenylcyclopenta[b]indol-3-yl)$_2$]Zirconium(IV) dichloide,

[dimethylsilanediyl(2,4-dimethyl-8-tolylcyclopenta[b]indol-3-yl)$_2$]zirconium(IV) dichloride,

[dimethylsilanediyl(2-methyl-4-phenyl-8-oxacyclopenta[a]inden-1-yl)$_2$]zirconium(IV) dichloride,

[dimethylsilanediyl(2-methyl-4-phenyl-8-telluracyclopenta[a]inden-1-yl)$_2$]zirconium dichloride,

[ethylene(2-methyl-8-phenylbenzo[b]cyclopenta[d]thien-3-ylidene)$_2$]zirconium(IV) dichloride,

[ethylene(2,5-dimethyl-8-phenylbenzo[b]cyclopenta[d]thien-3-ylidene)$_2$]zirconium(IV) dichloride,

[ethylene(2,5,8-trimethylbenzo[b]cyclopenta[d]thien-3-ylidene)$_2$]zirconium(IV) dichloride,

[ethylene(2-methyl-8-chlorobenzo[b]cyclopenta[d]thien-3-ylidene)$_2$]zirconium(IV) dichloide,

[ethylene(2-methyl-8-isopropylbenzo[b]cyclopenta[d]thien-3-ylidene)$_2$]zirconium(IV) dichloide,

[ethylene(2,8-dimethylbenzo[b]cyclopenta[d]thien-3-ylidene)$_2$]zirconium(IV) dichloride,

[diisopropylamidoborane(2-methyl-4-phenyl-8-oxacyclopenta[a]inden-1-yl)$_2$]zirconium(IV) dichloride,

[diisopropylamidoborane(2-methyl-8-phenylbenzo[b]cyclopenta[d]thien-3-ylidene)$_2$]zirconium(IV) dichloride,

[diisopropylamidoborane(2,5,8-trimethylbenzo[b]cyclopenta[d]thien-3-ylidene)$_2$]zirconium(IV) dichloride,

[diisopropylamidoborane(2,5-dimethyl-8-phenylbenzob-cyclopenta[d]thien-3-ylidene)$_2$]zirconium(IV) dichloride,

[diisopropylamidoborane(2,6,9-trimethylcyclopenta[a]naphthalen-3-ylidene)$_2$]zirconium(IV) dichloride,

[diisopropylamidoborane(2,4-dimethyl-8-tolylcyclopenta[b]indol-3-yl)$_2$]zirconium(IV) dichloride,

[methylene(2,4-dimethyl-8-tolylcyclopenta[b]indol-3-yl)$_2$]zirconium(IV) dichloride,

[methylene(2-methyl-4-phenyl-8-oxacyclopenta[a]inden-1-yl)$_2$]zirconium(IV) dichloride,

[methylene(2,6,9-trimethylcyclopenta[a]naphthalen-3-ylidene)$_2$]zirconium(IV) dichloride,

[methylene(2-methyl-8-phenylbenzo[b]cyclopenta[d]thien-3-ylidene)$_2$]zirconium(IV) dichloride,

[methylene(2-methyl-8-isopropylbenzo[b]cyclopenta[d]thien-3-ylidene)$_2$]zirconium(IV) dichloride,

[methylene(2-methyl-8-phenylbenzo[b]cyclopenta[d]thien-3-ylidene)-(2-isopropyl-4-phenyl-1H-inden-1-yl)]zirconium(IV) dichloride,

[diphenylmethylene(2-methyl-4-phenyl-8-oxacyclopenta[a]inden-1-yl)$_2$]zirconium(IV) dichloride,

[diphenylmethylene(2-methyl-8-isopropylbenzo[b]cyclopenta[d]thien-3-ylidene)$_2$]zirconium(IV) dichloride.

The numbering of the ring atoms is according to the following scheme:

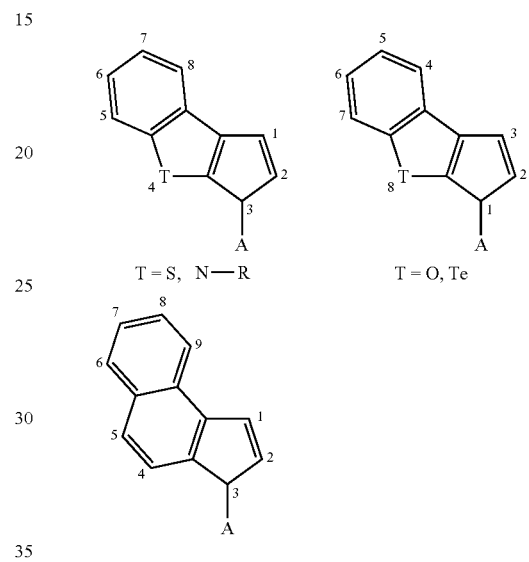

T = S, N—R    T = O, Te

The novel organometallic transition metal compounds of the formula (I) make it possible, in particular, to prepare propylene homopolymers having a reduced isotacticity, to prepare very propylene-rich propylene-ethylene rubber having a high molar mass and to prepare crystalline polyethylenes having high densities and high molecular weights.

The novel metallocenes of the formula (I) can be prepared by methods as described in WO 03045964. The organometallic transition metal compounds of the formula (I) are usually obtained together with a further diastereomer.

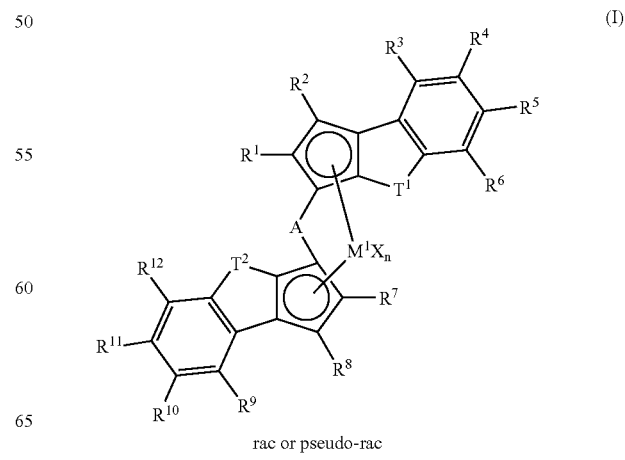

rac or pseudo-rac

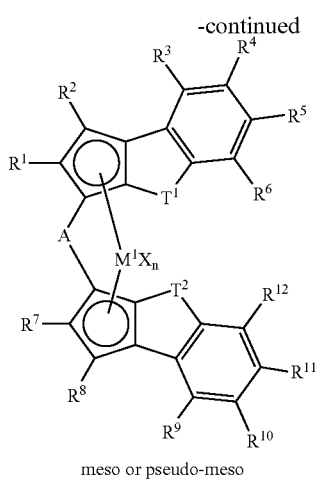

meso or pseudo-meso

The organometallic transition metal compounds of the formula (I) (rac or pseudo-rac) can also be used as a diastereomer mixture together with the undesired diastereomners (meso or pseudo-meso) coproduced in the synthesis in the preparation of the catalysts.

The separation of the diastereomers is known in principle.

The invention further provides biscyclopentadienyl ligand systems of the formula (II)

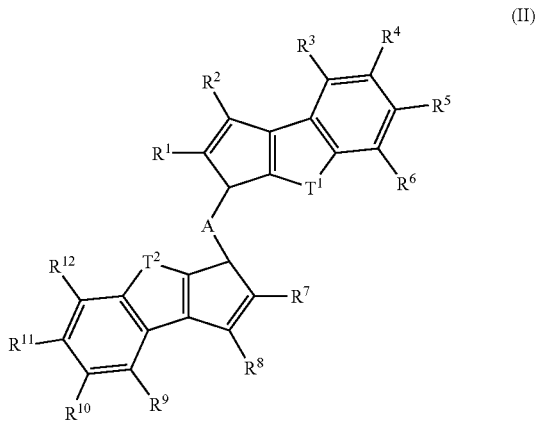

or their double bond isomers, where the variables $R^1$, $R^2$, $R^3$, $R^4$, $R^5$ $R^6$, $R^7$, $R^8$, $R^9$, $R^{10}$, $R^{11}$, $R^{12}$, $T^1$, $T^2$ and A are as defined in formula (I).

Particular preference is given to biscyclopentadienyl ligand systems of the formula (II)

in which $T^1$, $T^2$ are identical and are each —O—, —S—, —Se— or —Te—, preferably —O— or —S—, in particular —S—, $R^1$, $R^7$ are identical and are each a $C_1$-$C_{10}$-alkyl radical, for example methyl, ethyl, propyl, iso-propyl, n-butyl, n-hexyl, cyclohexyl or n-decyl, preferably methyl or ethyl, in particular methyl, $R^2$, $R^8$ are identical and are each hydrogen, $R^3$, $R^9$ are identical or different and are each a substituted or unsubstituted $C_6$-$C_{40}$-aryl radical or $C_2$-$C_{40}$-heteroaromatic radical having at least one heteroatom selected from the group consisting of O, N, S and P, preferably a substituted or unsubstituted $C_6$-$C_{40}$-aryl radical such as phenyl, 2-tolyl, 3-tolyl, 4-tolyl, 2,3-dimethylphenyl, 2,4-dimethylphenyl, 2,5-dimethylphenyl, 2,6-dimethylphenyl, 3,4-dimethylphenyl, 3,5-dimethylphenyl, 3,5-di(tert-butyl)phenyl, 2,4,6-trimethylphenyl, 2,3,4-trimethylphenyl, 1-naphthyl, 2-naphthyl, phenanthrenyl, p-isopropylphenyl, p-tert-butylphenyl, p-s-butylphenyl, p-cyclohexylphenyl and p-trimethylsilylphenyl, in particular phenyl, 1-naphthyl, 3,5-dimethylphenyl and p-tert-butylphenyl, $R^4$, $R^5$, $R^{10}$ and $R^{11}$ are identical and are each hydrogen, $R^6$, $R^{12}$ are identical and are each hydrogen or an organic radical having from 1 to 20 carbon atoms, for example a cyclic, branched or unbranched $C_1$-$C_{20}$—, preferably $C_1$-$C_{10}$-alkyl radical, a $C_2$-$C_{20}$—, preferably $C_2$-$C_8$-alkenyl radical, an arylalkyl radical having from 1 to 10, preferably from 1 to 4, carbon atoms in the alkyl part and from 6 to 14, preferably from 6 to 10, carbon atoms in the aryl part, preferably hydrogen, methyl, ethyl, n-propyl, isopropyl, n-butyl, i-butyl, s-butyl, t-butyl, phenyl, naphthyl, benzyl or 2-phenylethyl, in particular hydrogen, methyl or isopropyl, and A is a substituted silylene group or a substituted or unsubstituted ethylene group, preferably a substituted silylene group such as dimethylsilanediyl, methylphenylsilanediyl, methyl-tert-butylsilanediyl or diphenylsilanedlyl, in particular dimethylsilanediyl.

The substitution pattern of the biscyclopentadienyl ligand systems of the formula (II) is critical to the particular polymerization properties of the organometallic transition metal compounds containing these biscyclopentadienyl ligand systems.

The invention further provides for the use of a biscyclopentadienyl ligand system of the formula (II) for preparing an organometallic transition metal compound, preferably for preparing an organometallic transition metal compound of an element of group 4 of the Periodic Table of the Elements, in particular zirconium.

Thus, the present invention also provides a process for preparing an organometallic transition metal compound, which comprises reacting a biscyclopentadienyl ligand system of the formula (II) or a bisanion prepared therefrom with a transition metal compound. The usual procedure is firstly to doubly deprotonate a ligand system of the formula (II) by means of a base such as n-butyllithium and subsequently to react it with a suitable transition metal source such as zirconium tetrachloride. However, as an alternative, the uncharged biscyclopentadienyl ligand system of the formula (II) can be reacted directly with a suitable transition metal source which has strongly basic ligands, for example tetrakis(dimethylamino)zirconium.

The novel organometallic transition metal compounds of the formula (I) are, particularly in the presence of suitable cocatalysts, highly active catalyst constituents for the polymerization of olefins.

The cocatalyst which together with the novel organometallic transition metal compound of the formula (I) forms a polymerization-active catalyst system is able to convert the organometallic transition metal compound into a species which displays polymerization activity toward at least one olefin. The cocatalyst is therefore sometimes also referred to as activating compound. The polymerization-active transition metal species is frequently a cationic species. In this case, the cocatalyst is frequently also referred to as cation-forming compound.

The present invention therefore also provides a catalyst system for the polymerization of olefins comprising at least one organometallic transition metal compound of the formula (I) and at least one cocatalyst which is able to convert the organometallic transition metal compound into a species which displays polymerization activity toward at least one olefin.

Suitable cocatalysts or cation-forming compounds are, for example, compounds such as an aluminoxane, a strong uncharged Lewis acid, an ionic compound having a Lewis-acid cation or an ionic compound containing a Brönsted acid as cation. Preference is given to using an aluminoxane as cocatalyst.

In the case of metallocene complexes as organometallic transition metal compounds, the cocatalysts are frequently also referred to as compounds capable of forming metallocenium ions.

As aluminoxanes, it is possible to use, for example, the compounds described in WO 00/31090. Particularly useful compounds of this type are open-chain or cyclic aluminoxane compounds of the formula (III) or (IV)

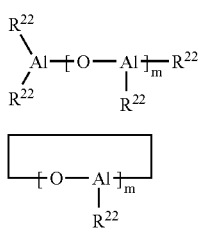

where $R^{22}$ is a $C_1$-$C_4$-alkyl group, preferably a methyl or ethyl group, and m is an integer from 5 to 30, preferably from 10 to 25.

These oligomeric aluminoxane compounds are usually prepared by reacting a solution of trialkylaluminum with water. In general, the oligomeric aluminoxane compounds obtained in this way are in the form of mixtures of both linear and cyclic chain molecules of various lengths, so that m may be regarded as a mean. The aluminoxane compounds can also be present in admixture with other metal alkyls, preferably aluminum alkyls.

Furthermore, it is also possible to use modified aluminoxanes in which some of the hydrocarbon radicals or hydrogen atoms have been replaced by alkoxy, aryloxy, siloxy or amide groups in place of the aluminoxane compounds of the formula (III) or (IV).

It has been found to be advantageous to use the novel organometallic transition metal compound of the formula (I) and the aluminoxane compounds in such amounts that the atomic ratio of aluminum from the aluminoxane compounds to the transition metal from the organometallic transition metal compound is in the range from 10:1 to 1000:1, preferably in the range from 20:1 to 500:1, in particular in the range from 30:1 to 400:1.

As strong, uncharged Lewis acids, preference is given to compounds of the formula (V)

$$M^3X^1X^2X^3 \quad (V)$$

where $M^3$ is an element of group 13 of the Periodic Table of the Elements, in particular B, Al or Ga, preferably B, $X^1$, $X^2$ and $X^3$ are each, independently of one another, hydrogen, $C_1$-$C_{10}$-alkyl, $C_6$-$C_{15}$-aryl, alkylaryl, arylalkyl, haloalkyl or haloaryl each having from 1 to 10 carbon atoms in the alkyl radical and from 6 to 20 carbon atoms in the aryl radical or fluorine, chlorine, bromine or iodine, in particular haloaryl, preferably pentafluorophenyl.

Further examples of strong, uncharged Lewis acids are given in WO 00/31090.

Particular preference is given to compounds of the formula (V) in which $X^1$, $X^2$ and $X^3$ are identical, preferably tris(pentafluorophenyl)borane.

Strong uncharged Lewis acids suitable as cocatalyst or cation-forming compounds also include the reaction products from the reaction of a boronic acid with two equivalents of a trialkylaluminum or the reaction products of the reaction of a trialkylaluminum with two equivalents of an acidic fluorinated, in particular perfluorinated, carbon compound such as pentafluorophenol or bis(pentafluorophenyl)borinic acid.

The suitable ionic compounds having Lewis-acid cations include salt-like compounds of the cation of the formula (VI)

$$[(Y^{a+})Q^1Q^2\ldots Q^z]^{d+} \quad (VI)$$

where

Y is an element of the groups 1 to 16 of the Periodic Table of the Elements, $Q^1$ to $Q^z$ are each single negatively charged groups such as $C_1$-$C_{28}$-alkyl, $C_6$-$C_{15}$-aryl, alkylaryl, arylalkyl, haloalkyl, haloaryl each having from 6 to 20 carbon atoms in the aryl radical and from 1 to 28 carbon atoms in the alkyl radical, $C_3$-$C_{10}$-cycloalkyl which may bear $C_1$-$C_{10}$-alkyl groups as substituents, halogen, $C_1$-$C_{28}$-alkoxy, $C_6$-$C_{15}$-aryloxy, silyl or mercaptyl groups, a is an integer from 1 to 6 and z is an integer from 0 to 5, and d corresponds to the difference a −z, but d is greater than or equal to 1.

Particularly useful cations are carbonium cations, oxonium cations and sulfonium cations and also cationic transition metal complexes. Particular mention may be made of the triphenylmethyl cation, the silver cation and the 1,1'-dimethylferrocenyl cation. They preferably have noncoordinating counterions, in particular boron compounds as are mentioned in WO 91/09882, preferably tetrakis(pentafluorophenyl)borate.

Salts having noncoordinating anions can also be prepared by combining a boron or aluminum compound, e.g. an aluminum alkyl, with a further compound which can react to link to two or more boron or aluminum atoms, e.g. water, and a third compound which forms an ionizing ionic compound with the boron or aluminum compound, e.g. triphenylchloromethane. In addition, a fourth compound which likewise reacts with the boron or aluminum compound, e.g. pentafluorophenol, can be added.

Ionic compounds containing Brönsted acids as cations preferably likewise have noncoordinating counterions. As Brönsted acid, preference is given to, in particular, protonated amine or aniline derivatives. Preferred cations are N,N-dimethylanilinium, N,N-dimethylcylohexylammonium and N,N-dimethylbenzylammonium and also derivatives of the latter two.

Preferred ionic compounds as cocatalysts or cation-forming compounds are, in particular, N,N-di-methylanilinium tetrakis(pentafluorophenyl)borate, N,N-dimethylcyclohexylammonium tetrakis-(pentafluorophenyl)borate and N,N-dimethylbenzylammonium tetrakis(pentafluorophenyl)borate.

It is also possible for two or more borate anions to be joined to one another, as in the dianion $[(C_6F_5)_2B-C_6F_4-B(C_6F_5)_2]^{2-}$, or the borate anion can be bound via a bridge having a suitable functional group to the surface of a support particle.

Further suitable cocatalysts or cation-forming compounds are listed in WO 00/31090.

The amount of strong, uncharged Lewis acids, ionic compounds having Lewis-acid cations or ionic compounds containing Brönsted acids as cations is usually from 0.1 to 20 equivalents, preferably from 1 to 10 equivalents, based on the novel organometallic transition metal compound of the formula (I).

Further suitable cocatalysts or cation-forming compounds are boron-aluminum compounds such as di-[bis(pentafluorophenylboroxy)]methylalane. Such boron-aluminum compounds are disclosed, for example, in WO 99/06414.

It is also possible to use mixtures of all the abovementioned cocatatalysts or cation-forming compounds. Preferred mixtures comprise aluminoxanes, in particular methylaluminoxane, and an ionic compound, in particular a compound containing the-tetrakis(pentafluorophenyl)borate anion, anchor a strong uncharged Lewis acid, in particular tris(pentafluorophenyl)borane.

Preference is given to using both the novel organometallic transition metal compound of the formula (I) and the cocatalysts or cation-forming compounds in a solvent, preferably aromatic hydrocarbons having from 6 to 20 carbon atoms, in particular xylenes and toluene.

The catalyst can further comprise a metal compound of the formula (VII),

$$M^4(R^{23})_r(R^{24})_s(R^{25})_t \quad (VII)$$

where $M^4$ is an alkali metal, an alkaline earth metal or a metal of group 13 of the Periodic Table, i.e. boron, aluminum, gallium, indium or thallium, $R^{23}$ is hydrogen, $C_1$-$C_{10}$-alkyl, $C_6$-$C_{15}$-aryl, alkylaryl or arylalkyl each having from 1 to 10 carbon atoms in the alkyl part and from 6 to 20 carbon atoms in the aryl part, $R^{24}$ and $R^{25}$ are identical or different and are each hydrogen, halogen, $C_1$-$C_{10}$-alkyl, $C_6$-$C_{15}$-aryl, alkylaryl, arylalkyl or alkoxy each having from 1 to 10 carbon atoms in the alkyl radical and from 6 to 20 carbon atoms in the aryl radical, is an integer from 1 to 3, and s and t are integers from 0 to 2, where the sum r+s+t corresponds to the valence of $M^4$, where the metal compound of the formula (VII) is usually not identical to the cocatalyst or the cation-forming compound. It is also possible to use mixtures of various metal compounds of the formula (VII).

Among the metal compounds of the formula (VII), preference is given to those in which $M^4$ is lithium, magnesium or aluminum and $R^{24}$ and $R^{25}$ are each $C_1$-$C_{10}$-alkyl.

Particularly preferred metal compounds of the formula (VII) are n-butyllithium, n-butyl-n-octyl-magnesium, n-butyl-n-heptyl-magnesium, tri-n-hexylaluminum, triisobutylaluminum, triethylaluminum and trimethylaluminum and mixtures thereof.

If a metal compound of the formula (VII) is used, it is preferably present in the catalyst in such an amount that the molar ratio of $M^4$ from formula (VII) to transition metal $M^1$ from the novel organometallic transition metal compound of the formula (I) is from 800:1 to 1:1, in particular from 200:1 to 2:1.

Particular preference is given to a catalyst system comprising a novel organometallic transition metal compound of the formula (I) and at least one cocatalyst and also a support.

To obtain such a supported catalyst system, the unsupported catalyst system can be reacted with a support. The order in which the support, the organometallic transition metal compound of the invention and the cocatalyst are combined is in principle immaterial. The organometallic transition metal compound of the present invention and the cocatalyst can be immobilized independently of one another or simultaneously. After the individual process steps, the solid can be washed with suitable inert solvents such as aliphatic or aromatic hydrocarbons.

As supports, preference is given to using finely divided supports which can be any organic or inorganic, inert solids. In particular, the support can be a porous solid such as talc, a sheet silicate, an inorganic oxide or a finely divided polymer powder (e.g. polyolefin).

Suitable inorganic oxides may be found among the oxides of the elements of groups 2, 3, 4, 5, 13, 14, 15 and 16 of the Periodic Table of the Elements. Examples of oxides preferred as support include silicon dioxide, aluminum oxide and mixed oxides of the elements calcium, aluminum, silicon, magnesium and titanium and also corresponding oxide mixtures. Other inorganic oxides which can be used alone or in combination with the abovementioned preferred oxidic supports are, for example, MgO, $ZrO_2$, $TiO_2$ or $B_2O_3$. A preferred mixed oxide is, for example, calcined hydrotalcite.

The support materials used preferably have a specific surface area in the range from 10 to 1 000 m²/g, a pore volume in the range from 0.1 to 5 ml/g and a mean particle size of from 1 to 500 μm. Preference is given to supports having a specific surface area in the range from 50 to 500 m²/g, a pore volume in the range from 0.5 to 3.5 ml/g and a mean particle size in the range from 5 to 350 μm. Particular preference is given to supports having a specific surface area in the range from 200 to 400 m²/g, a pore volume in the range from 0.8 to 3.0 ml/g and a mean particle size of from 10 to 100 μm.

The inorganic support can be subjected to a thermal treatment, e.g. to remove adsorbed water. Such a drying treatment is generally carried out at from 80 to 300° C., preferably from 100 to 200° C., with drying at from 100 to 200° C. preferably being carried out under reduced pressure and/or under a blanket of inert gas (e.g. nitrogen), or the inorganic support can be calcined at from 200 to 1000° C. to set, if desired, the desired structure of the solid and/or the desired OH concentration on the surface. The support can also be treated chemically using customary desiccants such as metal alkyls, preferably aluminum alkyls, chlorosilanes or $SiCl_4$ or else methylaluminoxane. Suitable treatment methods are described, for example, in WO 00/31090. The inorganic support material can also be chemically modified. For example, treatment of silica gel with $(NH_4)_2SiF_6$ leads to fluorination of the silica gel surface or treatment of silica gels with silanes containing nitrogen-, fluorine- or sulfur-containing groups leads to correspondingly modified silica gel surfaces.

Organic support materials such as finely divided polyolefin powders (e.g. polyethylene, polypropylene or polystyrene) can also be used and should likewise be freed of adhering moisture, solvent residues or other impurities by means of appropriate purification and drying operations before use. It is also possible to use functionalized polymeric supports, e.g. ones based on polystyrenes, via whose functional groups, for example ammonium or hydroxy groups, at least one of the catalyst components can be immobilized.

In a preferred form of the preparation of the supported catalyst system, at least one of the novel organometallic transition metal compounds of the formula (I) is brought into contact with at least one cocatalyst as activating or cation-forming compound in a suitable solvent, giving a soluble or insoluble, preferably soluble, reaction product, an adduct or a mixture.

The preparation obtained in this way is then mixed with the dehydrated or passivated support material, the solvent is removed and the resulting supported organometallic transition metal catalyst system is dried to ensure that all or most of the solvent is removed from the pores of the support material. The supported catalyst is usually obtained as a free-flowing powder. Examples of the industrial implementation of the above process are described in WO 96/00243, WO 98/40419 or WO 00/05277.

A further preferred embodiment comprises firstly applying the cocatalyst or the cation-forming compound to the support component and subsequently bringing this supported cocatalyst or this cation-forming compound into contact with the organometallic transition metal compound of the present invention.

Further useful cocatalyst systems are combinations obtained by combining the following components:

1st component: at least one defined boron or aluminum compound,

2nd component: at least one uncharged compound which has at least one acidic hydrogen atom, 3rd component at least one support, preferably an inorganic oxidic support, and optionally, as 4th component, a base, preferably an organic nitrogen-containing base, for example an amine, an aniline derivative or a nitrogen heterocycle.

The boron or aluminum compound used in the preparation of these supported cocatalysts is preferably a compound of the formula (VIII)

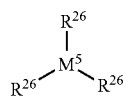

(VIII)

where $R^{26}$ are identical or different and are each hydrogen, halogen, $C_1$-$C_{20}$-alkyl, $C_1$-$C_{20}$-haloalkyl, $C_1$-$C_{10}$-alkoxy, $C_6$-$C_{20}$-aryl, $C_6$-$C_{20}$-haloaryl, $C_6$-$C_{20}$-aryloxy, $C_7$-$C_{40}$-arylalky, $C_7$-$C_{40}$-haloarylalkyl, $C_7$-$C_{40}$-alkylaryl, $C_7$-$C_{40}$-haloalkylaryl or $R^{26}$ is an $OSiR^{27}_3$ group, where $R^{27}$ are identical or different and are each hydrogen, halogen, $C_1$-$C_{20}$-alkyl, $C_1$-$C_{20}$-haloalkyl, $C_1$-$C_{10}$-alkoxy, $C_6$-$C_{20}$-aryl, $C_6$-$C_{20}$-haloaryl, $C_6$-$C_{20}$-aryloxy, $C_7$-$C_{40}$-arylalkyl, $C_7$-$C_{40}$-haloarylalkyl, $C_7$$C_{40}$-alkylaryl, $C_7$-$C_{40}$-haloalkylaryl, preferably hydrogen, $C_1$-$C_8$-alkyl or $C_7$-$C_{20}$-arylalkyl, and $M^5$ is boron or aluminum, preferably aluminum.

Particularly preferred compounds of the formula (VIII) are trimethylaluminum, triethylaluminum and triisobutylaluminum.

The uncharged compounds which have at least one acidic hydrogen atom and can react with compounds of the formula (VIII) are preferably compounds of the formulae (IX), (X) and (XI), $R^{28}$-D-H     (IX)

$(R^{28})_{3-h}$—B-(D-H)$_h$     (X)

H-D-$R^{29}$-D-H     (XI)

where $R^{28}$ are identical or different and are each hydrogen, halogen, a boron-free organic radical having from 1 to 40 carbon atoms, e.g. $C_1$-$C_{20}$-alkyl, $C_1$-$C_{20}$-haloalkyl, $C_1$-$C_{10}$-alkoxy, $C_6$-$C_{20}$-aryl, $C_6$-$C_{20}$-haloaryl, $C_6$-$C_{20}$-aryloxy, $C_7$-$C_{40}$-arylalky, $C_7$-$C_{40}$-haloarylalky, $C_7$-$C_{40}$-alkylaryl, $C_7$-$C_{40}$-haloalkylaryl, an $Si(R^{30})_3$ radical or a $CH(SiR^{30}_3)_2$ radical, where $R^{30}$ is a boron-free organic radical having from 1 to 40 carbon atoms, e.g. $C_1$-$C_{20}$-alkyl, $C_1$-$C_{20}$-haloalkyl, $C_1$-$C_{10}$-alkoxy, $C_6$-$C_{20}$-aryl, $C_6$-$C_{20}$-haloaryl, $C_6$-$C_{20}$-aryloxy, $C_7$-$C_{40}$-arylalky, $C_7$$C_{40}$-haloarylalky, $C_7$-$C_{40}$-alkylaryl, $C_7$-$C_{40}$-haloalkylaryl, and $R^{29}$ is a divalent organic group having from 1 to 40 carbon atoms, e.g. $C_1$-$C_{20}$-alkylene, $C_1$-$C_{20}$-haloalkylene, $C_6$-$C_{20}$-arylene, $C_6$-$C_{20}$-haloarylene, $C_7$-$C_{40}$-arylalkylene, $C_7$-$C_{40}$-haloarylalkylene, $C_7$-$C_{40}$-alkylarylene, $C_7$-$C_{40}$-haloalkylarylene, D is an element of group 16 of the Period Table of the Elements or an $NR^{31}$ group, where $R^{31}$ is hydrogen or a $C_1$-$C_{20}$-hydrocarbon radical such as $C_1$-$C_{20}$-alkyl or $C_6$-$C_{20}$-aryl, and D is preferably oxygen, and h 1 or 2.

Suitable compounds of the formula (IX) are water, alcohols, phenol derivatives, thiophenol derivatives or aniline derivatives, with halogenated alcohols and phenols being of particular importance and perfluorinated alkyls and phenols being of very particular importance. Examples of particularly useful compounds are pentafluorophenol, 1,1-bis-(pentafluorophenyl)methanol or 4-hydroxy-2,2',3,3',4',5,5',6,6'-nonafluorobiphenyl.

Suitable compounds of the formula (X) are boronic acids and borinic acids, in particular borinic acids having perfluorinated aryl radicals, for example $(C_6F_5)_2BOH$.

Suitable compounds of the formula (XI) are dihydroxy compounds in which the divalent carbon-containing group is preferably halogenated and particularly preferably perfluorinated. An example of such a compound is 4,4'-dihydroxy-2,2',3,3',5,5',6,6'-octafluorobiphenyl hydrate.

Examples of combinations of compounds of the formula (VIII) with compounds of the formula (IX) or (XI) are trimethylaluminum/pentafluorophenol, trimethylaluminum/1-bis-(pentafluorophenyl)-methanol, trimethylaluminum/4-hydroxy-2,2',3,3',4',5,5',6,6'-nonafluorobiphenyl, triethylaluminum/pentafluorophenol, triisobutylaluminum/pentafluorophenol and triethylaluminum/4,4'-dihydroxy-2,2',3,3',5,5',6,6'-octafluorobiphenyl hydrate, with, for example, reaction products of the following type being able to be formed:

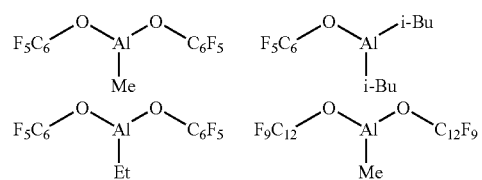

Examples of reaction products from the reaction of at least one compound of the formula (VIII) with at least one compound of the formula (X) are:

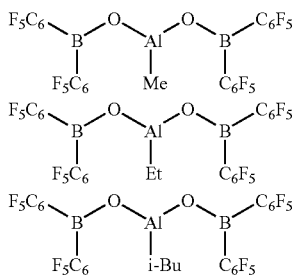

The order in which the components are combined is in principle immaterial.

If desired, the reaction products from the reaction of at least one compound of the formula (VIII) with at least one compound of the formula (IX), (X) or (XI) and optionally the organic nitrogen base may additionally be combined with an organometallic compound of the formula (III), (IV), (V) and/or (VII) in order then to form the supported cocatalyst system with the support.

In a preferred variant, the first component, e.g. compounds of the formula (VIII), is combined with the 2nd component, e.g. compounds of the formula (IX), (X) or (XI), and a support as 3rd component is combined separately with a base as 4th component and the two components are subsequently reacted with one another, preferably in an inert solvent or suspension medium. The supported cocatalyst formed can be freed of the inert solvent or suspension medium before it is reacted with the novel organometallic transition metal compound of the formula (I) and, if desired, a metal compound of the formula (VII) to form the catalyst system.

It is also possible firstly to prepolymerize the catalyst solid with x-olefins, preferably linear $C_2$-$C_{20}$-1-alkenes and in particular ethylene or propylene and then to use the resulting prepolymerized catalyst solid in the actual polymerization. The mass ratio of catalyst solids used in the prepolymerization to monomer polymerized onto it is usually in the range from 1:0.1 to 1:200.

Furthermore, a small amount of an olefin, preferably an α-olefin, for example vinylcyclohexane, styrene or phenyldimethylvinylsilane, as modifying component, an antistatic or a suitable inert compound such as a wax or oil can be added as additive during or after the preparation of the supported catalyst system. The molar ratio of additives to the organometallic transition metal compound of the present invention is usually from 1:1000 to 1000:1, preferably from 1:5 to 20:1.

The novel organometallic transition metal compounds of the formula (I) or the catalyst systems in which they are present are suitable for the polymerization or copolymerization of olefins.

The present invention therefore also provides a process for preparing polyolefins by polymerization or copolymerization of at least one olefin in the presence of a catalyst system comprising at least one of the novel organometallic transition metal compounds of the formula (I). In general, the catalyst system is used together with a further metal compound of the formula (VII), which may be different from the metal compound or compounds of the formula (VII) used in the preparation of the catalyst system, for the polymerization or copolymerization of olefins. The further metal compound is generally added to the monomer or the suspension medium and serves to free the monomer of substances which could adversely affect the catalyst activity. It is also possible to add one or more further cocatalytic or cation-forming compounds to the catalyst system in the polymerization process.

The olefins can be functionalized, olefinically unsaturated compounds such as ester or amide derivatives of acrylic or methacrylic acid, for example acrylates, methacrylates or acrylonitrile, or nonpolar olefinic compounds, including aryl-substituted α-olefins.

Preference is given to polymerizing olefins of the formula $R'''$—CH=CH—$R''$, where $R'''$ and $R''$ are identical or different and are each hydrogen or an organic radical, in particular a hydrocarbon radical having from 1 to 20 carbon atoms, in particular from 1 to 10 carbon atoms, or $R'''$ and $R''$ together with the atoms connecting them can form one or more rings.

Examples of such olefins are 1-olefins having from 2 to 40, preferably from 2 to 10, carbon atoms, e.g. ethylene, propylene, 1-butene, 1-pentene, 1-hexene, 1-heptene, 1-octene, 1-decene or 4-methyl-1-pentene, and unsubstituted or substituted vinylaromatic compounds such as styrene and styrene derivatives, and dienes such as 1,3-butadiene, 1,4-hexadiene, 1,7-octadiene, 5-ethylidene-2-norbornene, norbornadiene, ethylnorbornadiene and cyclic olefins such as norbornene, tetracyclododecene or methylnorbornene. Preference is given to ethylene, propylene, 1-butene, 1-hexene or 4-methyl-1-pentene.

The catalyst system of the present invention is particularly preferably used for homopolymerizing propylene or ethylene or copolymerizing ethylene with $C_3$-$C_8$-α-olefins such as propylene, 1-butene, 1-pentene, 1-hexene and/or 1-octene and/or cyclic olefins such as norbornene and/or dienes having from 4 to 20 carbon atoms, e.g. 1,4-hexadiene, norbornadiene, ethylidenenorbornene or ethylnorbornadiene, or, particularly preferably, copolymerizing propylene with ethylene and/or 1-butene. Examples of such copolymers are propylene-ethylene, propylen-1-butene, ethylene-1-butene, ethylene-1-hexene and ethylene-1-octene copolymers, and ethylene-propylene-ethylidenenorbornene and ethylene-propylene-1,4-hexadiene terpolymers.

The polymerization can be carried out in a known manner in bulk, in suspension, in the gas phase or in a supercritical medium in the customary reactors used for the polymerization of olefins. It can be carried out batchwise or preferably continuously in one or more stages. Solution processes, suspension processes, stirred gas-phase processes and gas-phase fluidized-bed processes are all possible. As solvent or suspension medium, it is possible to use inert hydrocarbons, for example isobutane, or else the monomers themselves.

The polymerization can be carried out at from −60 to 300° C. and at pressures in the range from 0.5 to 3 000 bar. Preference is given to temperatures in the range from 50 to 200° C., in particular from 60 to 100° C., and pressures in the range from 5 to 100 bar, in particular from 15 to 70 bar. The mean residence times are usually from 0.5 to 5 hours, preferably from 0.5 to 3 hours. Hydrogen can be used in the polymerization as molar mass regulator and/or to increase the activity. Furthermore, customary additives such as antistatics can also be used. The catalyst system of the present invention can be used directly in the polymerization, i.e. it is introduced in pure form into the polymerization system, or it can be admixed with inert components such as paraffins, oils or waxes to improve meterability.

The catalyst systems of the present invention are especially useful for preparing propylene homopolymers having a reduced isotacticity, i.e. reduced melting points, for preparing high molecular weight ethylene-propylene copolymers and for preparing high molecular weight polyethylenes. The catalyst system of the present invention makes it possible to prepare, for example in a two-stage cascade process, polymer mixtures which comprise a low-ethylene "propylene-ethylene rubber" as elastic phase in a crystalline polyethylene matrix.

The invention further provides the polyolefins obtainable by one of the abovementioned polymerization processes, in particular homopolymers and copolymers of propylene, and polyolefin compositions comprising the polyolefins obtainable by means of the catalyst systems of the present invention.

The polymers prepared by the process of the present invention and polyolefin compositions in which these are present are particularly useful for producing hard and stiff shaped bodies having a high ultimate tensile strength, e.g. fibers, filaments, injection-molded parts, films, plates or large hollow bodies (e.g. pipes), or are used, in particular, in plasticizer and lubricant formulations, melt adhesive applications, coatings, sealants, insulation, casting compositions or acoustic insulation materials.

The invention is illustrated by the following nonlimiting examples:

EXAMPLES

General Procedures:

The synthesis and handling of the organometallic compounds of the catalysts was carried out with exclusion of air and moisture under argon (glove box and Schlenk technique). All solvents used were purged with argon and dried over molecular sieves before use. Tetrahydrofuran (THF), diethyl ether and toluene were dried by refluxing for a number of hours over sodium/benzophenone, pentane over sodium/benzophenone/triglyme and dichloromethane over calcium hydride, subsequently distilled off and stored over 4A molecular sieves.

Methylalumoxane (solution in toluene; 30% by weight of MAO) was procured from Albemarle Corp. and Al(iso-Bu)$_3$ (1 M solution in toluene) was procured from Aldrich Chemical Company. Water-free heptane for the suspension polymerization was obtained by passing heptane through a column packed with 3A molecular sieves and a column packed with aluminum oxide. Eaton's reagent was used as procured commercially (Aldrich; 7% by weight phosphorus pentoxide in methanesulfonic acid).

4-Phenylbenzo[b]thiophene was synthesized by a method analogous to that of M. Kloezel et. al., *J. Organic Chem.*, 19, 1511 (1953).

Mass spectra were measured using a Hewlett Packard Series 6890 instrument equipped with a series 5973 mass analyzer (EI, 70 eV).

NMR spectra of organic and organometallic compounds were recorded at room temperature on a Varian Unity 300 NMR spectrometer. The chemical shifts are reported relative to SiMe$_4$.

Determination of the Melting Point:

The melting point $T_m$ was determined by DSC measurement in accordance with ISO Standard 3146 in a first heating phase at a heating rate of 20° C. per minute to 200° C., a dynamic crystallization at a cooling rate of 20° C. per minute down to 25° C. and a second heating phase at a heating rate of 20° C. per minute back to 200° C. The melting point was then the temperature at which the curve of enthalpy versus temperature measured in the second heating phase displayed a maximum.

Gel Permeation Chromatography

Gel permeation (GPC) was carried out at 145° C. in 1,2,4-trichlorobenzene using a Waters 150C GPC apparatus. The data were evaluated using the software Win-GPC from HS-Entwicklungsgesellschaft für wissenschaftliche Hard- und Software mbH, OberHilbersheim. The columns were calibrated by means of polypropylene standards having molar masses ranging from 100 to $10^7$ g/mol. Mass average ($M_w$) and number average ($M_n$) molar masses of the polymers were determined. The Q value is the ratio of mass average molar mass ($M_w$) to number average molar mass ($M_n$).

Determination of the Viscosity Number (I.V.):

The viscosity number was determined in decalin at 135° C. in an Ubbelohde viscometer PVS 1 with an S 5 measuring head (both from Lauda). For the sample preparation, 20 mg of polymer were dissolved in 20 ml of decalin at 135° C. over a period of 2 hours. 15 ml of the solution were placed in the viscometer; the instrument carried out a minimum of three running-out time measurements until a consistent result was obtained. The I.V. is calculated from the running-out times in accordance with I.V.=$(t/t_0-1)*1/c$, where t=mean of the running-out time of the solution, $t_0$=mean of the running-out time of the solvent, c=concentration of the solution in g/ml.

EXAMPLES

1. {Me$_2$Si(2-Me-8-Ph-benzo[b]cyclopenta[d]thien-3-yl)$_2$}ZrCl$_2$ (1)

1a) Synthesis of 2-methyl-8-phenyl-1,2-dihydrobenzo[b]cyclopenta[d]thiophen-3-one (1a)

A mixture of 10 g of 4-phenylbenzo[b]thiophene (47.6 mmol) and 4.8 ml of methacrylic acid (56.6 mmol) was added to 100 ml of Eaton's reagent over a period of 30 minutes, with the reaction temperature during the addition being 80° C. The reaction mixture was cooled to 60° C. and 400 ml of water were introduced slowly while stirring vigorously. The precipitated product was dissolved by addition of 250 ml of dichloromethane. After phase separation, the organic phase was washed with a saturated solution of sodium hydrogencarbonate and with water and subsequently dried over magnesium sulfate. The solvent was removed and 12 g of product were obtained. The product had a purity of 90% according to GC and consisted of two isomers present in a ratio of about 7:3 (thiophen-3-one:thiophen-1-one).

$^1$H-NMR of the main isomer (CDCl$_3$): δ=7.8 (d, 1H), 7.2-7.5 (m, 7H), 2.85 (m, 1H), 2.7 (d, 1H), 2.05 (d, 1H), 1.1 (d, 3H) ppm; EIMS: m/e (%)=278 ([M$^+$], 100), 263 (65), 249 (13), 234 (21), 221 (47), 202 (16), 189 (9), 176 (6), 163 (8), 151 (3), 139 (3).

1b) 2-Methyl-8-phenylbenzo[b]cyclopenta[d]thiophene (1b)

A solution of 81.4 g of 2-methyl-8-phenyl-1,2-dihydrobenzo[b]cyclopenta[d]thiophenone (0.29 mol) (1a) in 800 ml of THF was admixed at 0° C. with 225 ml of a 1.0 molar solution of lithium aluminum hydride (0.23 mol) in diethyl ether. The mixture was stirred at room temperature for another 4 hours. 25 ml of water were then carefully added and the resulting suspension was filtered through a layer of Celite and dried over magnesium sulfate. After filtration, the solvent was removed and a brown vitreous solid was obtained. The solid was dissolved in 400 ml of toluene and, after addition of 2.0 g of p-toluenesulfonic acid, stirred at 70° C. for 2 hours. The cooled reaction mixture was washed with a saturated solution of sodium hydrogencarbonate and with water and dried over magnesium sulfate. After the desiccant had been separated off, the solvent was removed and the residue was chromatographed on silica gel (5% methylene chloride in hexane as eluant). This gave 39 g (52%) of (1b) as a light-yellow oil.

$^1$H-NMR (CDCl$_3$) 2 isomers: δ=7.6 (m, 1H), 7.4 (m, 5H), 7.2 (m, 2H), 6.54 (s) and 5.8 (s) (1H total), 3.28 (s) and 2.79 (s) (2H total), 2.08 (s) and 2.02 (s) (3H total) ppm. EIMS: m/e (%)=262 (M$^+$, 100), 245 (21), 234 (5), 221 (16), 202 (10), 184 (5), 163 (3), 122 (5).

1c) Dimethyl-bis-(2-methyl-8-phenyl-3H-benzo[b]cyclopenta[d]thiophen-3-yl)silane (1c)

A solution of 19.0 g of 2-methyl-8-phenylbenzo[b]cyclopenta[d]thiophene (72.5 mmol) in 100 ml of tetrahydrofuran was cooled to −78° C. and admixed with 29 ml of a solution of n-butyllithium in hexane (2.5 M, 72.5 mmol). The reaction mixture was subsequently stirred at room temperature for 6 hours. The deep black solution was added dropwise at −78° C. to a solution of 4.66 g of dichlorodimethylsilane (36.2 mmol) in 50 ml of THF. The reaction mixture was subsequently slowly warmed to 50° C. and stirred for 16 hours. 10 ml of a saturated solution of ammonium chloride were slowly added, the phases were separated, the organic phase was dried over magnesium sulfate and the solvent was removed to give the crude product as a viscous oil. The crude product was chromatographed on silica gel (methylene chloride (20%)/hexane) to give 12.7 g (61%) of the silane (1c) as a viscous oil.

$^1$H-NMR (CDCl$_3$), several isomers: δ=7.7-7.9 (m, 2H); 7.3-7.6 (m, 10H); 7.1-7.3 (m, 4H); 6.05 (s), 5.95 (s), (1H total); 4.05 (s), 3.9 (s), 3.85 (s), (1 H total); 2.95 (s), 2.9 (s), (2H total); 1.95 (s), 2.05 (s), 2.1 (s), 2.15 (s), 2.2 (s), (6H total), −0.2 (m), 0.2 (s), 0.35 (s), (6H total) ppm.

1 Preparation of {Me$_2$Si(2-Me-8-Ph-benzo[b]cyclopenta[d]thien-3-yl)$_2$}ZrCl$_2$ (1)

A solution of 12.7 g of dimethyl-bis-(2-methyl-8-phenyl-3H-benzo[b]cyclopenta[d]thiophen-3-yl)-silane (21.9 mmol) in 200 ml of diethyl ether was cooled to −78° C. and admixed with 17.5 ml of a solution of n-butyllithium in hexane (2.5 M, 43.8 mmol). The reaction mixture was subsequently stirred at room temperature for 8 hours. The solvent was removed under reduced pressure. 5.1 g of zirconium tetrachloride (21.9 mmol) were added to the residue and the reaction mixture was suspended in 100 ml of hexane containing 2 ml diethyl ether and stirred at room temperature for 16 hours. The yellow solid was isolated with the aid of a frit which could be upended, the filtercake was washed with 20 ml of hexane and 20 ml of diethyl ether and dried under reduced pressure. This gave 16.7 g of crude product. 6 g of the crude product were stirred up in 150 ml of methylene chloride and the suspension was filtered through Celite. The filtrate was evaporated completely to give 4 g of crude metallocene having a rac /meso isomer ratio of about 40/60. The crude metallocene was stirred up in 30 ml of acetone and the solid was isolated by filtration. The filtercake was washed with pentane and dried under reduced pressure. This gave 0.6 g of the pure rac isomer.

Figure 1B:
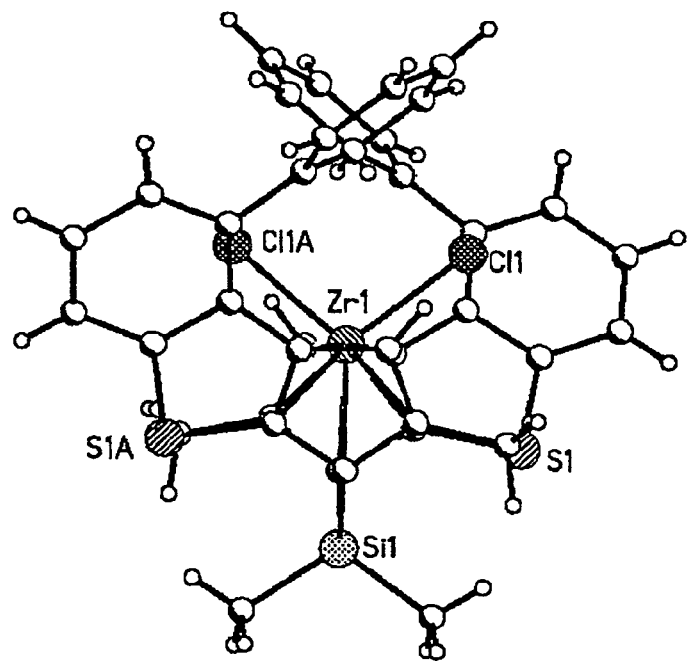

$^1$H-NMR (CDCl$_3$): δ=7.65 (m, 2H), 7.25-7.5 (m, 14H), 6.2 (s, 2H), 2.25 (s, 6H), 1.1 (s, 6H) ppm. X-ray structure analysis: FIGS. 1a and 1b show the structure of the compound (1) from different perspectives.

Example P1

Homopolymerization of Propene 4 ml of a solution of triisobutylaluminum in toluene (4 mmol, 1M) were placed in a dry 1 l reactor which had been flushed with nitrogen. At 30° C., 250 g of propylene were introduced and the contents of the reactor were heated to 65° C. A catalyst solution prepared by combining 0.6 mg of the metallocene (1) from Example 1 dissolved in 1.2 ml of toluene with 0.8 ml of a solution of methylaluminoxane in toluene (3.8 mmol, 30% by weight) and subsequently allowing the mixture to react for a further 10 minutes was introduced together with 50 g of propylene into the reactor. The contents of the reactor were stirred at 65° C. for 1 hour and the polymerization reaction was stopped by venting the reactor. The reactor cooled to room temperature during vaporization of the propane. After flushing the reactor with nitrogen for 10 minutes, 5 ml of methanol were added to the contents of the reactor. The polymer was taken from the reactor as a solution in toluene. After evaporation of the toluene solvent, the polymer was dried at 50° C. under reduced pressure for 2 hours. This gave 28.2 g of polypropylene. The results of the polymerization and the results of the polymer analysis are shown in Table 1 below.

Pentad analysis by means of the $^{13}$C-NMR spectrum: mmmm: 11.61%; mmmr: 13.91%; rmmr: 7.13%; mmrr: 8.97%; xmrx: 25.83%; rmrm: 19.78%; rrrr: 1.63%; rrrm: 4.90%; mrrm:6.24%. Triad analysis by means of the $^{13}$C-NMR spectrum: mm: 32.65%; mr: 54.57; rr:12.77%.

Example P2

Homopolymerization of Propene

The polymerization was carried out in a manner analogous to example P1. 4 ml of a solution of triisobutylaluminum in toluene (4 mmol, 1M) together with 250 g of propylene were placed in the reactor at 30° C. and the mixture was heated to 50° C. A catalyst solution prepared by combining 2.0 mg of the metallocene (1) from example 1 dissolved in 4 ml of toluene with 0.8 ml of a solution of methylalumoxane in (3.8 mmol, 30% by weight) and subsequently allowing the mixture to react for another 10 minutes was introduced together with 50 g of propylene into the reactor. The contents of the reactor were stirred at 50° C. for 0.5 hours. After the reaction had been stopped, the polymer was worked up to give 8 g of polypropylene. The results of the polymerization and the results of the polymer analysis are shown in table 1 below.

Example P3

Copolymerization of Propene with Ethene

The polymerization was carried out in a manner analogous to example P2. 4 ml of a solution of triisobutylaluminum in toluene (4 mmol,1M) were placed in a dry 1 l reactor which had been flushed with nitrogen. At 30° C., 250 g of propylene were introduced and the contents of the reactor were heated to 50° C. A catalyst solution prepared by combining 2.0 mg of the metallocene (1) from example 1 dissolved in 4 ml of toluene with 0.8 ml of a solution of methylalumoxane in toluene (3.8 mmol, 30% by weight) and subsequently allowing the mixture to react further for 10 minutes was introduced together with 50 g of propylene into the reactor. Ethylene was introduced into the reactor at a gauge pressure of 6 bar. The contents of the reactor were stirred at 50° C. for 0.5 hour, with the ethylene pressure being maintained by introduction of further ethylene. The reaction was stopped and the polymer was worked up to give 57 g of polymer. The results of the polymerization are shown in table 1 below.

Example P4

Copolymerization of Propene with Ethene

The polymerization was carried out in a manner analogous to example P3. 4 ml of a solution of triisobutylaluminum in toluene (4 mmol, 1M) together with 250 g of propylene were placed in the reactor at 30° C. and the mixture was heated to 50° C. A catalyst solution prepared by combining 2.0 mg of the metallocene (1) from example 1 dissolved in 4 ml of toluene with 0.8 ml of a solution of methylalumoxane in toluene (3.8 mmol, 30% by weight) and subsequently allowing the mixture to react further for 10 minutes was introduced together with 50 g of propylene into the reactor. Ethylene was introduced into the reactor at a gauge pressure of 12 bar. The contents of the reactor were stirred at 50° C. for 0.5 hour, with the ethylene pressure being maintained by introduction of further ethylene. The reaction was stopped and the polymer was worked up to give 117 g of polymer. The results of the polymerization are shown in table 1 below.

TABLE 1

| Example | Trans. metal comp. [mg] | Polym. time [h] | Ethene [bar] | Polym. temperature [° C.] | Activity [kg/(g * h)] | Viscosity number [dl/g] | Mw [kg/mol] | Q | Ethene content [% by weight] |
|---|---|---|---|---|---|---|---|---|---|
| P1 | 0.6 | 1.0 | 0 | 65 | 47 | 1.16 | 136 | 1.7 | 0 |
| P2 | 2.0 | 0.5 | 0 | 50 | 8 | 1.39 | | | 0 |
| P3 | 2.0 | 0.5 | 6 | 50 | 57 | 4.28 | | | 4 |
| P4 | 2.0 | 0.5 | 12 | 50 | 117 | 7.00 | | | 39 |

Units and abbreviations: activity in $kg_{polymer}/(g_{transition\ metal\ compound} * h_{polymerization\ time})$; weight average molar mass determined by GPC; polydispersity $Q = M_n/M_w$; ethene content determined by IR spectroscopy Example P5

Homopolymerization of Ethene 2 ml of a 1 molar solution of triisobutylaluminum in toluene (2 mmol) were placed in a dry 1 l reactor which had been flushed with nitrogen. At 30° C., 500 ml of dry heptane were introduced. A catalyst solution prepared by combining 0.1 mg of the metallocene (1) (0.135 µmol) from example 1 dissolved in 1.0 ml of toluene with 0.45 ml of a solution of methylalumoxane in toluene (0.7 mmol, 10% by weight) and subsequently allowing the mixture to react further for 10 minutes was introduced into the reactor. The reactor was heated to 80° C. and ethylene was introduced into the reactor at a gauge pressure of 10 bar. The contents of the reactor were stirred at 80° C. for 10 minutes and the polymerization reaction was stopped by venting the reactor. After cooling to room temperature, 5 ml of methanol were added to the contents of the reactor. The polymer was isolated and dried at 50° C. under reduced pressure for 4 hours. This gave 16.6 g of polyethylene. The results of the polymerization and the results of the polymer analysis are shown in table 2 below.

Example P6

Homopolymerization of Ethene

The polymerization was carried out in a manner analogous to example P5. 2 ml of a 1 molar solution of triisobutylaluminum in toluene (2 mmol) together with 500 ml of heptane were placed in the reactor at 30° C. A catalyst solution prepared by combining 0.1 mg of the metallocene (1) (0.135 µmol) from example 1 dissolved in 1.0 ml of toluene with 0.45 ml of a solution of methylalumoxane in toluene (0.7 mmol, 10% by weight) and subsequently allowing the mixture to react further for 10 minutes was introduced into the reactor. After heating to 80° C., ethylene was introduced into the reactor at a gauge pressure of 10 bar. The contents of the reactor were stirred at 80° C. for 20 minutes, with the ethylene pressure being maintained by introduction of further ethylene. The reaction was stopped and the polymer was worked up to give 18.7 g of polyethylene. The results of the polymerization and the results of the polymer analysis are shown in table 2 below.

Example P7

Homopolymerization of Ethene

The polymerization was carried out in a manner analogous to example P6. 2 ml of a 1 molar solution of triisobutylaluminum in toluene (2 mmol) together with 500 ml of heptane were placed in the reactor at 30° C. A catalyst solution prepared by combining 0.1 mg of the metallocene (1) (0.135 µmol) from example 1 dissolved in 1.0 ml of toluene with 0.45 ml of a solution of methylalumoxane in toluene (0.7 mmol, 10% by weight) and subsequently allowing the mixture to react further for 10 minutes was introduced into the reactor. After heating to 80° C., ethylene was introduced into the reactor at a gauge pressure of 10 bar. The contents of the reactor were stirred at 80° C. for 30 minutes, with the ethylene pressure being maintained by introduction of further ethylene. The reaction was stopped and the polymer was worked up to give 21.5 g of polyethylene. The results of the polymerization and the results of the polymer analysis are shown in table 2 below.

Comparative Example CP1

Homopolymerization of Ethene

The polymerization was carried out in a manner analogous to example P7. 2 ml of a 1 molar solution of triisobutylaluminum in toluene (2 mmol) together with 500 ml of heptane were placed in the reactor at 30° C. A catalyst solution prepared by combining 0.1 mg of ethylenebisindenylzirconium dichloride dissolved in 1.0 ml of toluene with 0.8 ml of a solution of methylalumoxane in toluene (1.2 mmol, 10% by weight) and subsequently allowing the mixture to react further for 10 minutes was introduced into the reactor. After heating to 80° C., ethylene was introduced into the reactor at a gauge pressure of 10 bar. The contents of the reactor were stirred at 80° C. for 30 minutes, with the ethylene pressure being maintained by introduction of further ethylene. The reaction was stopped and the polymer was worked up to give 11.8 g of polyethylene. The results of the polymerization and the results of the polymer analysis are shown in table 2 below.

Example P8

Homopolymerization of Ethene in the Presence of Hydrogen

The polymerization was carried out in a manner analogous to example P7. 2 ml of a 1 molar solution of trilsobutylaluminum in toluene (2 mmol) together with 500 ml of heptane were placed in the reactor at 30° C. A catalyst solution prepared by combining 0.1 mg of the metallocene (1) from example 1 dissolved in 1.0 ml of toluene with 0.45 ml of a solution of methylalumoxane in toluene (0.7 mmol, 10% by weight) and subsequently allowing the mixture to react further for 10 minutes was introduced into the reactor. 100 ml of hydrogen were passed into the reactor. After heating to 80° C., ethylene was introduced into the reactor at a gauge pressure of 10 bar. The contents of the reactor were stirred at 80° C. for 30 minutes, with the ethylene pressure being maintained by introduction of further ethylene. The reaction was stopped and the polymer was worked up to give 12.6 g of polyethylene. The results of the polymerization and the results of the polymer analysis are shown in table 2 below.

TABLE 2

| Example | Trans. metal comp. [mg] | Polym. time [h] | Hydrogen [ml] | Polymer yield [g] | Activity [kg/(g * h)] | Viscosity number [dl/g] | Melting point [° C.] |
|---|---|---|---|---|---|---|---|
| P5 | 0.1 | ⅙ | 0 | 13.6 | 816 | 14.7 | 141 |
| P6 | 0.1 | ⅓ | 0 | 18.7 | 562 | 13.8 | 141 |
| P7 | 0.1 | ½ | 0 | 21.5 | 430 | 15.7 | 144 |
| CP1 | 0.1 | ½ | 0 | 11.8 | 236 | 1.1 | 143 |
| P8 | 0.1 | ½ | 100 | 12.6 | 252 | 1.14 | 140 |

All polymerizations of ethylene were carried out in heptane (500 ml) in the presence of 2 mmol of TiBA at 80° C. and 10 bar of ethene pressure; the ratio of $Al_{MAO}/Zr_{TMC}$ was about 5 270;
Units and abbreviations: activity in $kg_{polymer}/(g_{transition\ metal\ compound} * h_{polymerization\ time})$

We claim:

1. A catalyst system for the polymerization of olefins, comprising at least one organometallic transition metal compound and at least one cocatalyst which is able to convert the organometallic transition metal compound into a species which displays polymerization activity toward at least one olefin, wherein the organometallic transition metal compound has the formula (I)

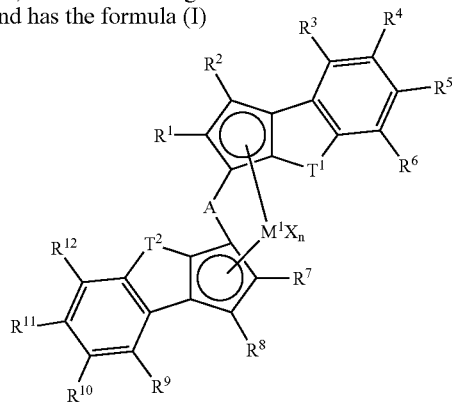

where
M$^1$ is a Group 4 element,
X are identical or different and are each an organic or inorganic radical, where two radicals X can also be joined to one another,
n is 2,
R$^1$, R$^7$ are identical and are each a $C_1$-$C_{10}$ alkyl radical,
R$^3$, R$^9$ are identical or different and are each a substituted or unsubstituted $C_6$-$C_{40}$ aryl radical or $C_2$-$C_{40}$ heteroaromatic radical containing at least one heteroatom selected from the group consisting of O, N, S and P,
R$^6$, R$^{12}$ are identical and are each hydrogen or an organic radical having from 1 to 20 carbon atoms,
and
A is a substituted silylene group or a substituted or unsubstituted ethylene group.

2. The catalyst system of claim 1 further comprising a support.

3. The catalyst system of claim 1 wherein M$^1$ is zirconium.

4. The catalyst system of claim 1 wherein R$^1$ and R$^7$ are each methyl.

5. The catalyst system of claim 1 wherein R$^3$ and R$^9$ are each a substituted or unsubstituted $C_6$-$C_{40}$ aryl radical.

6. The catalyst system of claim 1 wherein A is dimethylsilanediyl.

* * * * *

UNITED STATES PATENT AND TRADEMARK OFFICE
CERTIFICATE OF CORRECTION

PATENT NO. : 7,504,354 B2  Page 1 of 1
APPLICATION NO. : 10/578059
DATED : March 17, 2009
INVENTOR(S) : Michael J. Elder et al.

It is certified that error appears in the above-identified patent and that said Letters Patent is hereby corrected as shown below:

In claim 1, delete: " 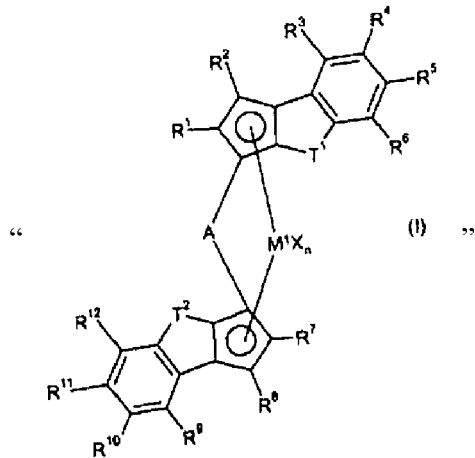 (I) " Insert: -- 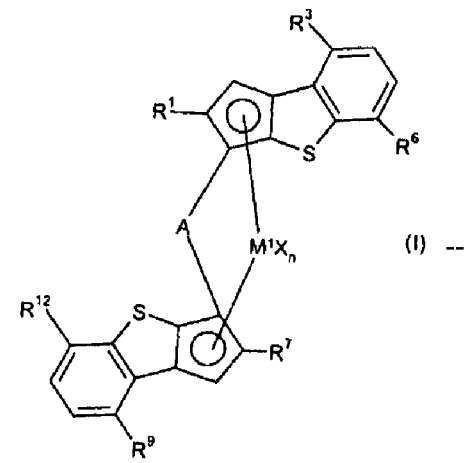 (I) --

Signed and Sealed this

Tenth Day of November, 2009

David J. Kappos
*Director of the United States Patent and Trademark Office*